(12) United States Patent
Elzein et al.

(10) Patent No.: US 7,407,960 B2
(45) Date of Patent: Aug. 5, 2008

(54) SUBSTITUTED HETEROCYCLIC COMPOUNDS

(75) Inventors: Elfatih Elzein, Fremont, CA (US); Dmitry Koltun, Foster City, CA (US); Jeff Zablocki, Mountain View, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 11/518,085

(22) Filed: Sep. 7, 2006

(65) Prior Publication Data
US 2007/0004751 A1 Jan. 4, 2007

Related U.S. Application Data

(62) Division of application No. 10/729,499, filed on Dec. 5, 2003, now Pat. No. 7,125,876.

(60) Provisional application No. 60/431,506, filed on Dec. 5, 2002.

(51) Int. Cl.
*A61K 31/496* (2006.01)
*C07D 263/56* (2006.01)
*C07D 277/64* (2006.01)

(52) U.S. Cl. .................. 514/254.02; 544/368

(58) Field of Classification Search ................ 544/368; 514/254.02
See application file for complete search history.

(56) References Cited

U.S. PATENT DOCUMENTS 4,788,306 A * 11/1988 Schiehser et al. ........... 549/549
6,573,264 B1 * 6/2003 Zablocki et al. ............ 514/249

2001/0047000 A1 * 11/2001 Wolff et al. ............ 514/252.12

FOREIGN PATENT DOCUMENTS

WO 2002064576 * 8/2002

OTHER PUBLICATIONS

Sato et al. Chem.Pharm. Bull. vol. 20,pp. 905-917 (1972).*
McCormick et al. Gen Pharmac. vol. 30, p. 639-645 (1998).*
Zacharowski et al. European Journal of Pharmacology, vol. 418, p. 105-110 (2001).*

* cited by examiner

*Primary Examiner*—Emily Bernhardt
(74) *Attorney, Agent, or Firm*—Brian Lewis; Michael J. Beck

(57) ABSTRACT

Disclosed are novel heterocyclic compounds having the structure

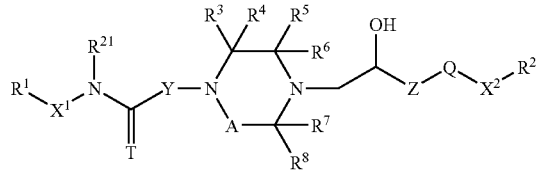

which are useful for the treatment of various disease states, in particular cardiovascular diseases such as atrial and ventricular arrhythmias, intermittent claudication, Prinzmetal's (variant) angina, stable and unstable angina, exercise induced angina, congestive heart disease, and myocardial infarction. The compounds are also useful in the treatment of diabetes.

11 Claims, No Drawings

SUBSTITUTED HETEROCYCLIC COMPOUNDS

This application is a Divisional Application of U.S. patent application Ser. No. 10/729,499, filed Dec. 5, 2003, which issued Oct. 24, 2006, as U.S. Pat. No. 7,125,876, and claimed priority to U.S. Provisional Patent Application Ser. No. 60/431,506, filed Dec. 5, 2002, the complete disclosure of which is hereby incorporated by reference.

FIELD OF THE INVENTION

The present invention relates to novel heterocyclic derivatives, and to their use in the treatment of various disease states, in particular cardiovascular diseases such as atrial and ventricular arrhythmias, intermittent claudication, Prinzmetal's (variant) angina, stable and unstable angina, exercise induced angina, congestive heart disease, ischemia, reperfusion injury, myocardial infarction and diabetes. The invention also relates to methods for their preparation, and to pharmaceutical compositions containing such compounds.

BACKGROUND

Certain classes of piperazine compounds are known to be useful for the treatment of cardiovascular diseases, including arrhythmias, angina, myocardial infarction, and related diseases such as intermittent claudication and diabetes. For example, U.S. Pat. No. 4,567,264 discloses a class of substituted piperazine compounds that includes a compound known as ranolazine, (±)-N-(2,6-dimethylphenyl)-4-[2-hydroxy-3-(2-methoxyphenoxy)-propyl]-1-piperazineacetamide, and its pharmaceutically acceptable salts, and their use in the above disease states.

Despite the desirable properties demonstrated by ranolazine, which is a very effective cardiac therapeutic agent, believed to function as a fatty acid oxidation inhibitor, there remains a need for compounds that have similar therapeutic properties to ranolazine, but are more potent and have a longer half-life.

SUMMARY OF THE INVENTION

It is an object of this invention to provide novel substituted heterocyclic compounds that are fatty acid oxidation inhibitors with good therapeutic half-lives. Accordingly, in a first aspect, the invention relates to compounds of Formula I:

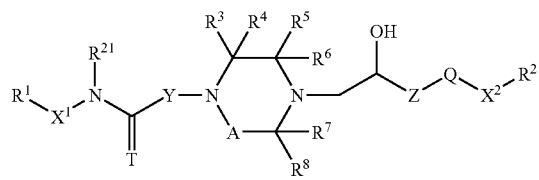

wherein:
  $R^1$ and $R^2$ are independently optionally substituted alkyl, optionally substituted alkenyl, optionally substituted alkynyl, optionally substituted cycloalkyl, optionally substituted aryl, optionally substituted heterocycle, or optionally substituted heteroaryl;
  $X^1$ is a covalent bond, or $-(CR^{15}R^{16})_p-$, in which $R^{15}$ and $R^{16}$ are independently hydrogen, hydroxy, lower alkyl, or $-C(O)OR^{17}$, in which $R^{17}$ is hydrogen, lower alkyl, or optionally substituted phenyl, and p is 1, 2 or 3;
    with the proviso that when p is 1, $R^{15}$ and $R^{16}$ cannot be hydroxy;
  $R^{21}$ is hydrogen or lower alkyl;
  T is oxygen or sulfur;
  Y and Z are $-(CR^{18}R^{19})_q-$ and q at each occurrence is 1, 2 or 3, in which $R^{18}$ and $R^{19}$ at each occurrence is hydrogen or lower alkyl.
  A is $-(CR^9R^{10})_m-$; in which m is 1 or 2; and
  $R^3$, $R^4$, $R^5$, $R^6$, $R^7$, $R^8$, $R^9$, and $R^{10}$ at each occurrence are hydrogen, lower alkyl, or $-C(O)R$; in which R is $-OR^{11}$ or $-NR^{11}R^{12}$, where $R^{11}$ and $R^{12}$ are hydrogen or lower alkyl; or
  $R^3$ and $R^4$, $R^5$ and $R^6$, $R^7$ and $R^8$, $R^9$ and $R^{10}$, when taken together with the carbon to which they are attached, represent carbonyl; or
  $R^3$ and $R^7$, or $R^3$ and $R^9$, or $R^5$ and $R^7$, or $R^5$ and $R^9$, when taken together form a bridging group $-(CR^{13}R^{14})_n-$, in which n is 1, 2 or 3, and $R^{13}$ and $R^{14}$ are independently hydrogen or lower alkyl;
    with the proviso that the maximum number of carbonyl groups is 1; the maximum number of $-C(O)R$ groups is 1; and the maximum number of bridging groups is 1;
  Q is oxygen, sulfur, or $-NR^{20}-$, in which $R^{20}$ is hydrogen or optionally substituted lower alkyl;
  $X^2$ is a covalent bond or $-(CR^{18}R^{19})_q-$ wherein q at each occurrence is 1, 2 or 3, and $R^{18}$ and $R^{19}$ at each occurrence is hydrogen or lower alkyl;
    with the proviso that when $X^1$ is a covalent bond and Y is $-(CR^{18}R^{19})_q-$ in which q is 1 and $R^{18}$ and $R^{19}$ are hydrogen, then $R^1$ is not optionally substituted phenyl.

A second aspect of this invention relates to pharmaceutical formulations, comprising a therapeutically effective amount of a compound of Formula I and at least one pharmaceutically acceptable excipient.

A third aspect of this invention relates to a method of using the compounds of Formula I in the treatment of a disease or condition in a mammal that is treatable by a fatty acid oxidation inhibitor. Such diseases include, but are not limited to, protection of skeletal muscles against damage resulting from trauma, intermittent claudication, shock, diabetes and cardiovascular diseases including atrial and ventricular arrhythmias, intermittent claudication, Prinzmetal's (variant) angina, stable angina, unstable angina, exercise induced angina, congestive heart disease, and myocardial infarction. The compounds of Formula I can also be used to preserve donor tissue and organs used in transplants.

A fourth aspect of this invention relates to methods of preparing the compounds of Formula I.

Of the compounds of Formula I, one preferred class includes those compounds in which A is methylene, particularly those compounds in which $R^3$, $R^4$, $R^6$, $R^7$, $R^8$, $R^9$, and $R^{10}$ are hydrogen and $R^5$ is hydrogen or methyl. A preferred group within this class includes those compounds in which Q and T are both oxygen and $X^2$ is a covalent bond.

A preferred subgroup includes those compounds of Formula I in which $R^{21}$ is hydrogen, Y is methylene or ethylene, and Z is methylene. Preferred members of this subgroup include those compounds of Formula I in which $R^1$ is optionally substituted aryl or optionally substituted heteroaryl and $R^2$ is optionally substituted heteroaryl, especially where $R^2$ is optionally substituted benzothiazolyl or optionally substituted benzoxazolyl, and $X^1$ is a covalent bond, methylene, or $-CH(CH_3)-$.

At present, preferred compounds of the invention include.

2-{4-[(2R)-2-hydroxy-3-(2-methylbenzothiazol-5-yloxy) propyl]piperazinyl}-N-indan-4-ylacetamide;

2-{4-[(2R)-2-hydroxy-3-(2-methylbenzothiazol-5-yloxy) propyl]piperazinyl}-N-((1S)(1,2,3,4-tetrahydronaphthyl)) acetamide;

2-{4-[(2R)-2-hydroxy-3-(2-methylbenzothiazol-5-yloxy) propyl]piperazinyl}-N-((1S)-1-(2-naphthyl)ethyl)acetamide;

2-{4-[(2R)-2-hydroxy-3-(2-methylbenzothiazol-5-yloxy) propyl]piperazinyl}-N-((1S)-1-phenylethyl)acetamide;

2-{4-[(2R)-2-hydroxy-3-(2-methylbenzothiazol-5-yloxy) propyl]piperazinyl}-N-[4-(4-chlorophenyl)(1,3-thiazol-2-yl)]acetamide;

2-{4-[(2R)-2-hydroxy-3-(2-methylbenzothiazol-5-yloxy) propyl]-3-methylpiperazinyl}-N-[4-(4-chlorophenyl)(1,3-thiazol-2-yl)]acetamide;

2-{4-[(2R)-2-hydroxy-3-(2-methylbenzothiazol-5-yloxy) propyl]piperazinyl}-N-(9-ethylcarbazol-3-yl)acetamide;

2-{4-[(2R)-2-hydroxy-3-(2-phenylbenzoxazol-5-yloxy) propyl]piperazinyl}-N-(6-quinolyl)acetamide; and 2-{4-[(2R)-2-hydroxy-3-(2-methylbenzothiazol-5-yloxy) propyl]piperazinyl}-N-(8-quinolyl)acetamide.

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or 2) an alkyl group as defined above that is interrupted by 1-10 atoms independently chosen from oxygen, sulfur and NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or 3) an alkyl group as defined above that has both 1, 2, 3, 4 or 5 substituents as defined above and is also interrupted by 1-10 atoms as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1, 2, or 3 substituents, as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, preferably having from 1 to 20 carbon atoms, preferably 1-10 carbon atoms, more preferably 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, preferably having from 1, 2, 3, 4, 5, or 6 carbon atoms.

The term "substituted alkylene" refers to:

(1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or (2) an alkylene group as defined above that is interrupted by 1-20 atoms independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both 1, 2, 3, 4 or 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH (NHMe)CH$_2$—), 2-carboxypropylene isomers(—CH$_2$CH (CO$_2$H)CH$_2$—), ethoxyethyl (—CH$_2$CH$_2$O—CH$_2$CH$_2$—), ethylmethylaminoethyl (—CH$_2$CH$_2$N(CH$_3$) CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or propynyl, —C≡CCH$_3$), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, cycloaklyl, aryl, heteroaryl, heterocyclyl or where both R groups are joined to form a heterocyclic group (e.g., morpholino). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "ester" or "carboxyester" refers to the group —C(O)OR, where R is alkyl, cycloalkyl, aryl, heteroaryl, or heterocyclyl, which may be optionally further substituted by alkyl, alkoxy, halogen, CF$_3$, amino, substituted amino, cyano, or —S(O)$_n$R$_a$, in which R$_a$ is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl, anthryl, tetrahydronaphthyl, indanes, and the like). Preferred aryls include phenyl and naphthyl.

Unless otherwise constrained by the definition for the aryl substituent, such aryl groups can optionally be substituted with 1, 2, 3, 4 or 5 substituents, preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y-Z, in which Y is optionally substituted alkylene and Z is alkenyl, cycloalkenyl, or alkynyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, $CF_3$, amino, substituted amino, cyano, or —$S(O)_nR$, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl,—SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1, 2, or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl (an alkyl ester), arylthio, heteroaryl, heteroarylthio, heterocyclylthio, thiol, alkylthio, aryl, aryloxy, aralkyl, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazolyl, benzothienyl, benzoxazolyl). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, 9-ethylcarbazole, carboline, phenanthridine, acridine, phenanthroline, thiazole, isothiazole, phenazine, oxazole, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —$S(O)_2R$, in which R is alkyl, aryl, or heteroaryl. "Substituted sulfone" refers to a group —$S(O)_2R$, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, and polymorphs and prodrugs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:

(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

In many cases, the compounds of this invention are capable of forming acid and/or base salts by virtue of the presence of amino and/or carboxyl groups or groups similar thereto.

The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The naming and numbering of the compounds of the invention is illustrated with a representative compound of Formula I in which $R^1$ is cyclohexyl, $R^2$ is 2-methyl-benzothiazol-5-yl, $R^3$, $R^4$, $R^5$, $R^6$, $R^7$, and $R^8$ are hydrogen, A is —$(CR^9R^{10})_m$, in which $R^9$ and $R^{10}$ are hydrogen and m is 1, $R^{21}$ is hydrogen, Q and T are both oxygen, $X^1$ and $X^2$ are both covalent bonds, Y is —$(CR^{18}R^{19})_q$, in which $R^{18}$ and $R^{19}$ are hydrogen and q is 1, and Z is $C(R^{18}R^{19})_q$, in which $R^{18}$ and $R^{19}$ are hydrogen and q is 1;

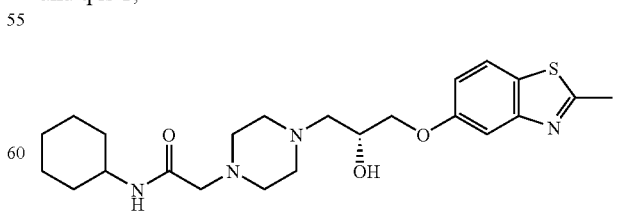

which is named 2-{4-[(2R)-2-hydroxy-3-(2-methylbenzothiazol-5-yloxy)propyl]piperazinyl}-N-cyclohexylacetamide.

Synthesis of the Compounds of Formula I

One method of preparing the compounds of Formula I is shown in Reaction Scheme I.

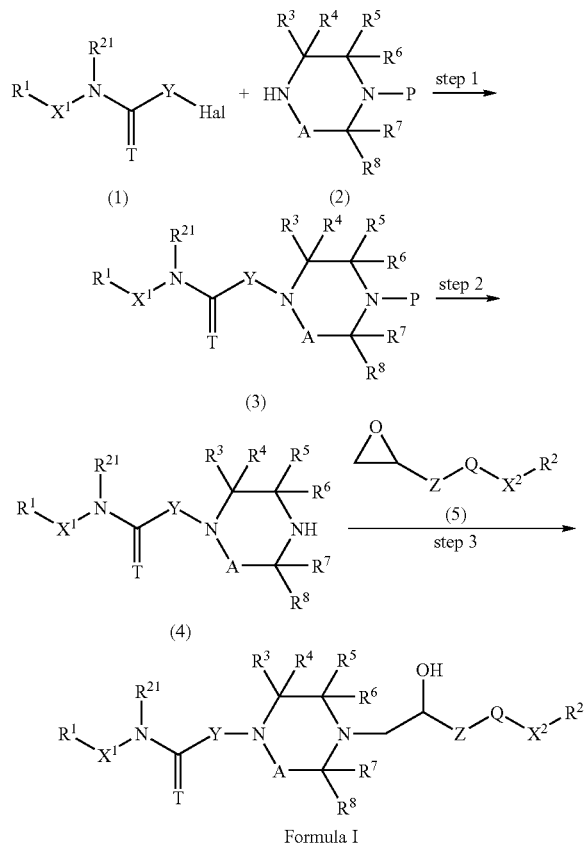

in which A, $R^1$, $R^2$, $R^3$, $R^4$, $R^5$, $R^6$, $R^7$, $R^8$, $R^{21}$, T, $X^1$, $X^2$, Y, and Z are as defined in the Summary of the Invention, P is a protecting group (for example BOC or CBZ), and Hal is halogen.

Step 1—Preparation of a Compound of Formula (3).

The compound of formula (3) is prepared conventionally by reaction of a compound of formula (1) with a compound of formula (2), which is commercially available from, for example, Aldrich. In general, the two compounds are reacted in an inert solvent, for example acetone, in the presence of a tertiary organic base, for example triethylamine, or an inorganic base, for example potassium carbonate. The reaction is conducted at a temperature of about reflux, for about 8-48 hours, preferably overnight. When the reaction is substantially complete, the product of formula (3) is isolated and purified by conventional means, for example by chromatography on silica gel.

Step 2—Preparation of a Compound of Formula (4).

A. Preparation of Formula (4) when the Protecting Group P is Carbobenzyloxy.

The compound of formula (3) where P is carbobenzyloxy is deprotected by hydrogenation under pressure in an inert solvent, for example methanol at 30 psi of hydrogen, in the presence of a catalyst, for example Pd/C. The reaction is conducted at about 0-30° C., preferably at about room temperature, for about 8-48 hours, preferably 24 hours. When the reaction is substantially complete, the product of formula (4) is isolated and purified by conventional means.

B. Preparation of Formula (4) when the Protecting Group P is 1-tert-butoxycarbonyl The compound of formula (3) where P is t-butoxycarbonyl is deprotected by acid hydrolysis. In general, the compound of formula (3) is dissolved in an inert solvent, for example methylene chloride, and a strong acid added, for example trifluoroacetic acid. The reaction is conducted at about 0-30° C., preferably at about room temperature, for about 8-48 hours, preferably overnight. When the reaction is substantially complete, the product of formula (4) is isolated and purified by conventional means.

Step 3—Preparation of a Compound of Formula I

The compound of formula (4) is then reacted with a compound of formula (5), which is commercially available, or is prepared for example as shown in Reaction Scheme V. The reaction is conducted in an inert solvent, for example ethanol. The reaction is conducted at about 30-100° C., preferably at about reflux, for about 8-48 hours, preferably 24 hours. When the reaction is substantially complete, the product of Formula I is isolated and purified by conventional means, for example by preparative thin layer chromatography.

An alternative preparation of a compound of Formula I is shown in Reaction Scheme II, where P is BOC or CBZ.

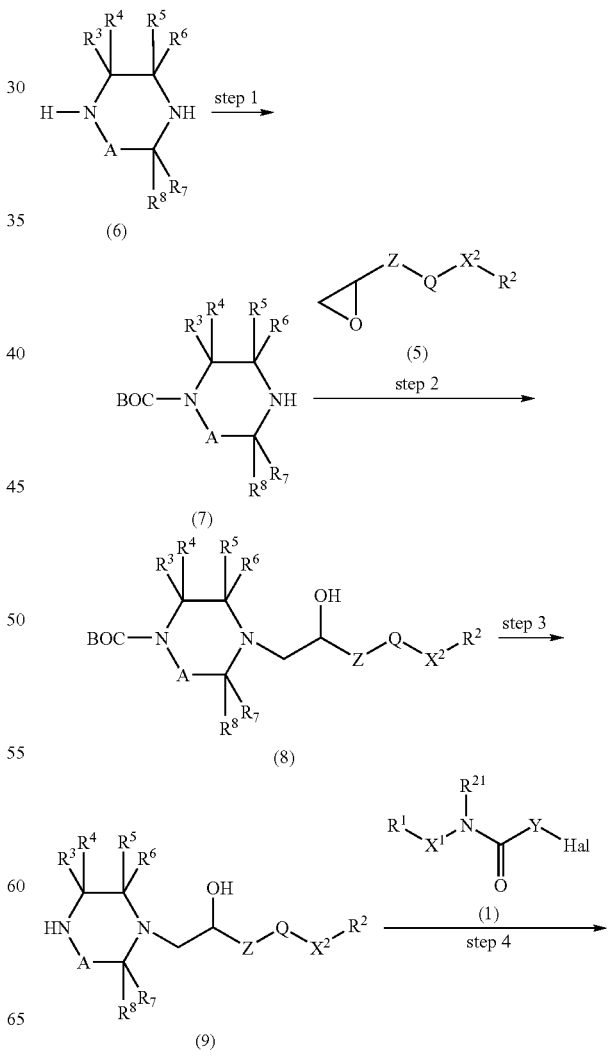

-continued

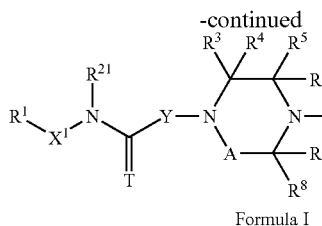

Formula I

Step 1. Preparation of a Compound of Formula (7).

The compound of formula (6) is protected, for example by reaction with 1-(tert-butoxycarbonyl)-2-tert-butyl-3-methyl-4-imidazolidinone (BOC-ON). The reaction is conducted in an organic solvent, for example, chloroform, for about 15 hours at room temperature in the presence of a tertiary organic base, for example triethylamine. When the reaction is substantially complete, the product of formula (7) is isolated and purified by conventional means, for example, by column chromatography.

Step 2. Preparation of a Compound of Formula (8).

The protected compound of formula (7) is reacted with a compound of formula (5), which is commercially available, or is prepared for example as shown in Reaction Scheme V. In general, the reaction is carried out in an inert solvent, for example methylene chloride, optionally in the presence of a catalyst, for example ytterbium (III)trifluoromethane-sulfonate. The reaction is conducted at about 0-30° C., preferably at about room temperature, for about 8-48 hours, preferably overnight, if in the presence of a catalyst. In the absence of a catalyst, the mixture is refluxed for a similar period of time in ethanol in the presence of triethylamine. When the reaction is substantially complete, the product of formula (8) is isolated and purified by conventional means, for example by chromatography of the residue on silica gel.

Step 3—Preparation of a Compound of Formula (9)

The compound of formula (8) is then deprotected. In general, the compound of formula (8) is dissolved in an inert solvent, for example methylene chloride, and a strong acid is added, for example trifluoroacetic acid. The reaction is conducted at about 0-30° C., for example at about room temperature, for about 8-48 hours, preferably overnight. When the reaction is substantially complete, the product of formula (9) is isolated and purified by conventional means.

Step 4—Preparation of a Compound of Formula I

The compound of formula (9) is then reacted with a compound of formula (1). In general, the two compounds are mixed in an inert solvent, for example ethanol, in the presence of an inorganic or tertiary organic base, for example potassium carbonate or triethylamine. The reaction is conducted at about 30-100° C., preferably at about reflux, for about 8-48 hours, preferably overnight. When the reaction is substantially complete, the product of Formula I is isolated and purified by conventional means, for example by chromatography.

The above synthesis may be used to prepare racemic mixtures or optically active isomers of the compounds of Formula I, by starting with optically active intermediates.

C. Alternative Preparation of a Compound of Formula I.

An alternative preparation of a compound of Formula I using a resin-mediated procedure is shown in Reaction Scheme III.

REACTION SCHEME III

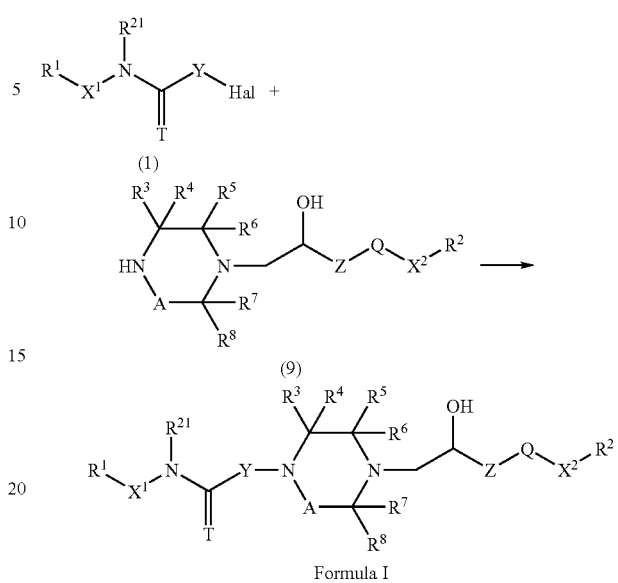

Formula I

In general, a compound of formula (1) and a compound of formula (9) are placed into a vial and diluted with an organic solvent, for example dichloroethane. A resin, for example polystyrene-diisopropylethylamine (PS-DIEA) resin, is added, and the vial shaken at about 60-120° C., preferably at about 80° C., for 6-24 hours, preferably overnight. After cooling to room temperature, a mixture of resins, for example, PS-Isocyanate resin and PS-Trisamine resin are added and shaken at about 10-25° C., preferably room temperature and then maintained at about 60-120° C., preferably 80° C., from 6-24 hours, preferably overnight. After cooling to room temperature, the contents of the vial are transferred into a frit-fitted syringe, filtered, washed with additional organic base, for example dichloroethane repeatedly. After concentration, for example, by Speedvac™ the crude mixture is purified and analyzed by standard means. The compound of Formula I is isolated as a free base using standard methodology.

The above Reaction Schemes for Formula I may be used to prepare racemic mixtures of optically active isomers of the compounds of Formula I.

Preparation of Compounds of Formula (1)

The compounds of formula (1) can be made by conventional methods well known to those of ordinary skill in the art. For example, the synthesis of a compound of formula (1) where $X^1$ is a covalent bond is shown in Reaction Scheme IVA. Synthesis of the compound of formula (1) where $X^1$ is other than a covalent bond is shown in Reaction Scheme IVB. Synthesis of a compound of formula (1) where $X^1$ is $(CR^{15}R^{16})_p$, in which $R^{16}$ is —C(O)OR$^{17}$, is shown in Reaction Scheme IVC.

A. Preparation of a Compound of Formula (1) where $X^1$ is a Covalent Bond.

REACTION SCHEME IVA

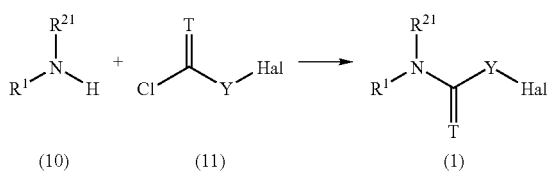

(10)   (11)   (1)

In general, an amine of formula (10), which are commercially available, is reacted with a compound of formula (11), which is either commercially available or may be made by methods well known to those skilled in the art, in an inert solvent, for example ethyl ether, in the presence of a base, for example sodium bicarbonate. The mixture is stirred at about −10° C. to 10° C., for example about 0° C., for about 1-3 hours, preferably 2 hours and then for a further 30 minutes to 4 hours, preferably 1 hour, at room temperature. The product of formula (1) is isolated by conventional means.

B. Preparation of a Compound of Formula (1) where $X^1$ is other than a Covalent Bond.

The preparation of a compound of formula (1) where $X^1$ is other than a covalent bond is shown in Reaction Scheme IVB.

REACTION SCHEME IVB

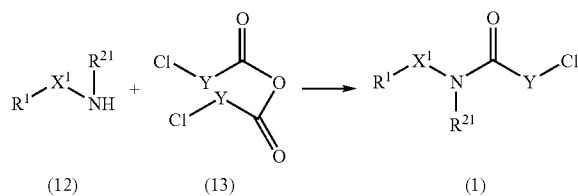

(12)  (13)  (1)

To a mixture of an appropriate amine of formula (12) and a chloroanhydride of formula (13), both of which are commercially available, in an inert solvent, for example tetrahydrofuran, is added a base, for example triethylamine. The mixture is allowed to stir for 30 minutes to 4 hours, for example about 1 hour, at about 0° C., and for an additional 30 minutes to 2 hours, preferably about 1 hour, at about room temperature. The solvent is removed, and the product of formula (1) is isolated by conventional means.

C. Preparation of a Compound of Formula (1) where $X^1$ is $(CR^{15}R^{16})_p$, in which $R^{16}$ is $—C(O)OR^{17}$ The preparation of a compound of formula (1) where $X^1$ is $(CR^{15}R^{16})_p$, in which $R^{16}$ is $—C(O)OR^{17}$, is shown in Reaction Scheme IVC.

REACTION SCHEME IVC

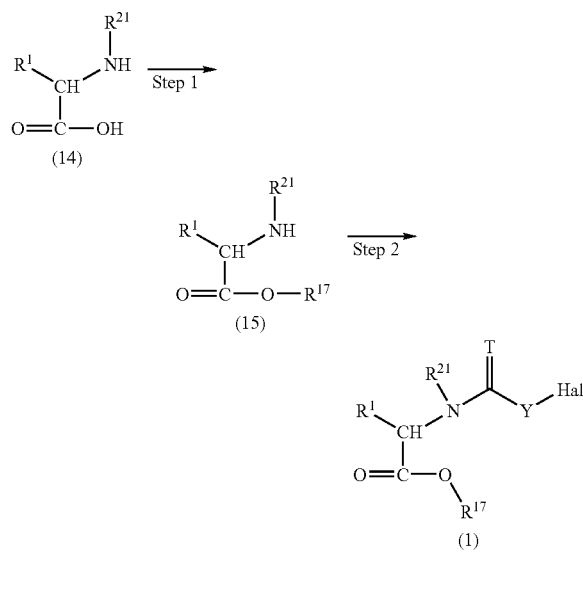

Step 1. Preparation of a Compound of Formula (15)

The compound of formula (15) is prepared by conventional esterification of a compound of formula (14). In general, the compound of formula (14) is reacted with an alcohol, for example ethanol, at about 0° C., in the presence of an acid, for example hydrochloric acid gas. The mixture is stirred for about 8-24 hours, for example overnight. When the reaction is substantially complete, the product of formula (15) is isolated by conventional means, for example by chromatography on silica gel.

Step 2. Preparation of a Compound of Formula (1).

The ester of formula (15) is dissolved in an inert solvent, for example tetrahydrofuran, and reacted with an anhydride of formula (13), for example chloroacetic anhydride, in the presence of a base, preferably a hindered amine, for example, diisopropylethylamine. The reaction is conducted under an inert atmosphere, for example nitrogen, at about 0-30° C., preferably about room temperature, for about 8-24 hours, preferably overnight. When the reaction is substantially complete, the product of formula (1) is isolated and purified by conventional means, for example by chromatography of the residue on silica gel.

Preparation of a Compound of Formula (5).

The preparation of an epoxide of formula (5) in which Q is oxygen is shown in Reaction Scheme V.

REACTION SCHEME V

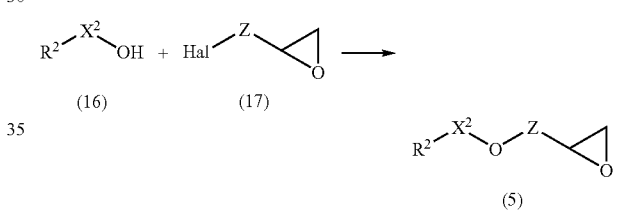

The compounds of formula (16) and (17) are either commercially available or can be made by conventional methods well known to those of ordinary skill in the art. The compound of formula (5) is prepared conventionally by reaction of a compound of formula (16) with an epoxide of formula (17) in an inert solvent, for example acetone, in the presence of a tertiary organic base or an inorganic base, for example potassium carbonate, at a temperature of about 40-75° C., preferably about reflux temperature, for about 8-48 hours, for example overnight. When the reaction is substantially complete, the product of formula (5) is isolated and purified by conventional means, for example by chromatography of the residue on silica gel. Alternatively, after filtration the product can be crystallized from the filtrate.

A specific example of a preparation of a compound of formula (16) in which $X^2$ is ethylene is shown in Reaction Scheme IVF below, illustrated by an example in which Q is oxygen and R is 2-phenylthiazol-4-yl.

REACTION SCHEME VI

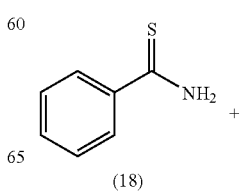

(18)

-continued

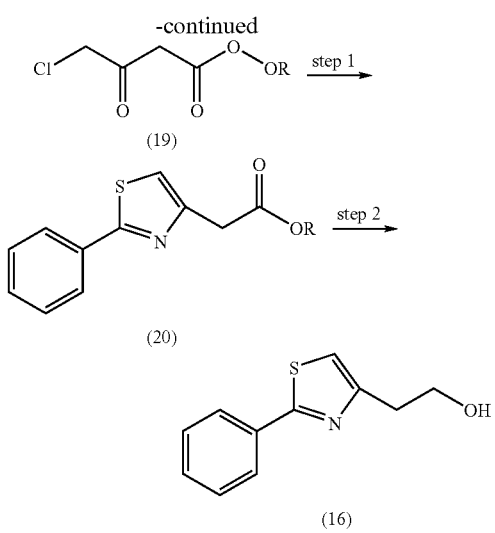

Step 1—Preparation of Formula (20)

Benzthioamide (18) is reacted with a 4-chloro-3-oxobutanoate ester of formula (19), for example ethyl 4-chloro-3-oxobutanoate, at a temperature of about 120° C., for about 2 hours. When the reaction is substantially complete, the product, a 2-(2-phenyl-1,3-thiazol-4-yl)acetate ester, is isolated by conventional means, and the residue purified, for example by chromatography on silica gel, to provide a compound of formula (20).

Step 2—Preparation of Formula (16)

The compound of formula (20) is then reduced conventionally, for example with lithium aluminum hydride in ether, to provide an alcohol of formula (16) (2-(2-phenyl-1,3-thiazol-4-yl)ethan-1-ol in the example shown above).

This alcohol is then reacted as shown above in Reaction Scheme V with a haloepoxide of formula (17) to provide a compound of formula (5), which is then converted into a compound of Formula I as shown in Reaction Scheme I.

Compounds where $X^2$ is methylene or propylene are made by similar methods.

General Utility

The compounds of Formula I are effective in the treatment of conditions known to respond to administration of fatty acid oxidation inhibitors, including diabetes, protection of skeletal muscles against damage resulting from trauma, intermittent claudication, shock, and cardiovascular diseases including atrial and ventricular arrhythmias, Prinzmetal's (variant) angina, stable angina, unstable angina, ischemia and reperfusion injury in cardiac, kidney, liver and the brain, congestive heart disease, and myocardial infarction. The compounds of Formula I can also be used to preserve donor tissue and organs used in transplants, and may be coadministered with thrombolytics, anticoagulants, and other agents.

Testing

Activity testing is conducted as described in those patents and patent applications referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modern Pharmaceutics", Marcel Dekker, Inc. 3$^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Compounds of Formula I may be impregnated into a stent by diffusion, for example, or coated onto the stent such as in a gel form, for example, using procedures known to one of skill in the art in light of the present disclosure.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The Formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be Formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix Formulations. Examples of controlled release systems are given in U.S. Pat. Nos. 3,845,770; 4,326,525; 4,902514; and 5,616,345. Another Formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are for example Formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and are generally administered in a pharmaceutically effective amount. For example, for oral administration, each dosage unit contains from 1 mg to 2 g of a compound of Formula I, and for parenteral administration, for example from 0.1 to 700 mg of a compound of Formula I. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preFormulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. For example the compositions are administered by the oral or nasal respiratory route for local or systemic effect. Compositions in for example pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, for example orally or nasally, from devices that deliver the Formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound Formula (1)

A. Preparation of a Compound of Formula (1) in which $X^1$ is a Covalent Bond, T is Oxygen, Y is $CH_2$, $R^1$ is 2-Methylbenzothiazol-5-yl, $R^{21}$ is Hydrogen, and Hal is Chloro

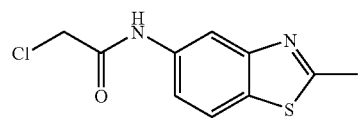

2-Methylbenzothiazole-5-ylamine (1.0 g, 4.2 mm) was suspended in a mixture of 1:1 ethyl ether: saturated aqueous sodium bicarbonate. To the suspension was added chloracetyl chloride (0.7 g, 6.5 mm) over a period of 10 minutes. The mixture was allowed to stir at room temperature for 24 hours, and then diluted with 50 ml of ethyl acetate. The organic layer was separated, dried over magnesium sulgate, and filtered. The solvent was evaporated from the filtrate, and the white solid residue obtained was triturated in ether and filtered, to afford 2-chloro-N-(2-methylbenzothiazol-5-yl)acetamide, a compound of formula (1).

B. Preparation of a Compound of Formula (1) in which $X^1$ and Y are both $CH_2$, T is Oxygen, $R^1$ is 2,6-Difluorophenyl, T is Oxygen, $R^{21}$ is Hydrogen., and Hal is Chloro

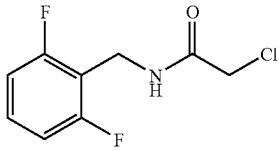

To a mixture of 2,6-difluorobenzylamine (3 g, 21.4 mmol) and chloroacetic anhydride (1.5 g, 14 mmol) in tetrahydrofuran (100 mL) was added triethylamine (3 mL, 30 mmol). The mixture was allowed to stir for 1 hour at 0° C. and for additional 1 hour at room temperature. The solvent was removed and ether (100 mL) was added to the residue. The ether layer was washed twice with 10% citric acid (50 mL), dried over $MgSO_4$ and filtered. The solvent was removed to afford N-[(2,6-difluorophenyl)methyl]-2-chloroacetamide, a compound of formula (1), as a white solid.

C. Preparation of a Compound of Formula (1) in which $X^1$ is a Covalent Bond, T is Oxygen, $R^1$ is 2,6-Dimethylphenyl, $R^{21}$ is Hydrogen, Y is —$CH_2CH_2$—, and Hal is Bromo

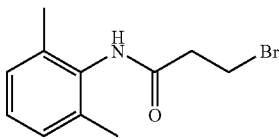

To a mixture of 2,6-dimethylaniline (2 g, 16.5 mmol), diethyl ether, and aqueous saturated sodium bicarbonate (50:50 v/v) was added dropwise 3-bromopropionoyl chloride (2 g, 19.8 mm) in ether (5 mL). The mixture was allowed to stir at 0° C. for 2 hours, and at room temperature for an additional 1 hour. The organic layer was washed with 10% citric acid, dried over $MgSO_4$, then filtered. The solvent was evaporated to afford N-(2,6-dimethylphenyl)-3-bromopropanamide, a compound of formula (1), as a white solid.

D. Preparation of a Compound of Formula (1) varying $R^1$, $X^1$, Y and Hal

Similarly, following the procedure of 1A, 1B, or 1C above, but optionally replacing the amine with other amines of formula (10), and optionally replacing the acid halide with other compounds of formula (11), the following compounds of formula (1) were prepared:

2-chloro-N-(benzothiazol-2-yl)acetamide;
2-chloro-N-(5-chlorobenzoxazol-2-yl)acetamide;
2-chloro-N-(4-chlorobenzoxazol-2-yl)acetamide;
2-chloro-N-(1-methylbenzimidazol-2-yl)acetamide;
2-chloro-N-(4-chlorobenzothiazol-2-yl)acetamide;
2-chloro-N-cyclohexylacetamide;
2-chloro-N-cyclohexyl-N-methylacetamide;
2-chloro-N-cyclopentylacetamide;
2-chloro-N-methylethylacetamide;
2-chloro-N-(bicyclo[2.2.1]hept-2-yl)acetamide;
2-chloro-N-(5-methylisoxazol-3-yl)acetamide;
2-chloro-N-(indan-5-yl)acetamide;
2-chloro-N-naphth-1-ylacetamide;
2-chloro-N-(4-chloronaphth-1-yl)acetamide;
2-chloro-N-(2-pyrrolylphenyl)acetamide;
2-chloro-N-(5,6-dimethylbenzothiazol-2-yl)acetamide;
2-chloro-N-(3-quinolinyl)acetamide;
2-chloro-N-(2-methyl-4-quinolinyl)acetamide;
2-chloro-N-(5-quinolinyl)acetamide;
2-chloro-N-(6-quinolinyl)acetamide;
2-chloro-N-(7-quinolinyl)acetamide;
2-chloro-N-(8-quinolinyl)acetamide;
2-chloro-N-(1H-indazol-5-yl)acetamide;
2-chloro-N-(2-fluorophenyl)acetamide;
2-chloro-N-benzylacetamide;
2-chloro-N-adamant-2-ylacetamide;
2-chloro-N-(5,6,7,8-tetrahydronaphthyl)acetamide;
2-chloro-N-((1R)5,6,7,8-tetrahydronaphthyl)acetamide;
2-chloro-N-((1S)5,6,7,8-tetrahydronaphthyl)acetamide;
2-chloro-N-(4-fluoro-(5,6,7,8-tetrahydronaphthyl)acetamide;
2-chloro-N-(benzo[2,3-c]1,2,5-thiadiazol-4-yl)acetamide;
2-chloro-N-(2-methylphenyl)acetamide;
2-chloro-N-(3-methylphenyl)acetamide;
2-chloro-N-(4-methylphenyl)acetamide;
2-chloro-N-(2-hydroxyindanyl)acetamide;
2-chloro-N-((1S,2R)-2-hydroxyindanyl)acetamide;
2-chloro-N-((1S,2R)-4-fluoro-2-hydroxyindanyl)acetamide;
2-chloro-N-((1S)-indanyl)acetamide;
2-chloro-N-((1R)-indanyl)acetamide;
2-chloro-N-(2H,3H-benzo[e]1,4-dioxin-6-yl)acetamide;
2-chloro-N-(2H,3H-benzo[e]1,4-dioxin-5-yl)acetamide;
2-chloro-N-(indan-2-yl)acetamide;
2-chloro-N-(indan-4-yl)acetamide;
2-chloro-N-(indan-5-yl)acetamide;
2-chloro-N-(benzotriazolyl)acetamide;
2-chloro-N-(indol-4-yl)acetamide;
2-chloro-N-((1S)-4-chloroindanyl)acetamide;
2-chloro-N-(chroman-4-yl)acetamide;
2-chloro-N-(2,6,6-trimethylbicyclo[3.1.1]hept-3-yl)acetamide;
2-chloro-N-((5S,3R)-2,6,6-trimethylbicyclo[3.1.1]hept-3-yl)acetamide;
2-chloro-N-(1-naphthylethyl)acetamide;
2-chloro-N-(2-naphthylethyl)acetamide;
2-chloro-N-(2,6-difluorophenylmethyl)acetamide;
2-chloro-N-(cyclohexylmethyl)acetamide;
2-chloro-N-(2,2-dimethylpropyl)acetamide;
2-chloro-N-(2,2-diphenylethyl)acetamide;
2-chloro-N-(3-(methylphenylamino)propyl)acetamide; and
2-chloro-N-(2,4-dichlorophenylmethyl)acetamide.
2-chloro-N-(2,4-dichlorophenylethyl)acetamide;
2-chloro-N-(3,4-dichlorophenylmethyl)acetamide;
2-chloro-N-(4-chlorophenylmethyl)acetamide;
2-chloro-N-(3,5-difluorophenylmethyl)acetamide;
2-chloro-N-(3-fluorophenylmethyl)acetamide;
2-chloro-N-(2-fluorophenylmethyl)acetamide
2-chloro-N-(2,4-difluorophenylmethyl)acetamide;
2-chloro-N-(2,6-difluorophenylmethyl)acetamide;
2-chloro-N-(2,5-difluorophenylmethyl)acetamide;
2-chloro-N-(3,4-difluorophenylmethyl)acetamide;
2-chloro-N-(3-chlorophenylmethyl)acetamide;
2-chloro-N-(2-phenylethyl)acetamide;
2-chloro-N-((1R)-1-phenylethyl)acetamide;
2-chloro-N-((1S)-1-phenylethyl)acetamide;
2-chloro-N-(4-fluorophenylethyl)acetamide;
2-chloro-N-((1S)-2-hydroxy-1-phenylethyl)acetamide;
2-chloro-N-((1R)-2-hydroxy-2-phenylethyl)acetamide;
2-chloro-N-((2S,1R)-2-hydroxy-1-methyl-2-phenylethyl)acetamide;
2-chloro-N-((1S,2R)-2-hydroxy-1-methyl-2-phenylethyl)acetamide;

2-chloro-N-(1-acetylindolin-7-yl)acetamide;
2-chloro-N-(9-ethylcarbazol-3-yl)acetamide.
N-benzothiazol-2-yl-3-bromopropionamide
3-bromo-N-(1-methylbenzimidazol-2-yl)propionamide;
3-bromo-N-(6-chlorobenzoxazol-2-yl)propionamide;
3-bromo-N-(4-chlorobenzothiazol-2-yl)propionamide;
N-(2,6-dimethylphenyl)-3-bromopropanamide;
3-bromo-N-(7-chlorobenzothiazol-2-yl)propionamide;
3-bromo-N-cyclohexylpropionamide;
3-bromo-N-cyclopentylpropionamide;
N-(5,6-dimethylbenzothiazol-2-yl)-3-bromopropionamide;
N-((2S,1R)-2-hydroxyindanyl)-3-bromopropionamide;
N-((1S)indanyl)-3-bromopropionamide;
N-bicyclo[2.2.1]hept-2-yl-3-bromopropionamide;
3-bromo-N-(5-methylisoxazol-3-yl)propionamide;
N-(2,2-dimethylpropyl)-3-bromopropionamide;
N-adamantanyl-3-bromopropionamide;
N-((1S)-(1,2,3,4-tetrahydronaphthyl))-3-bromopropionamide;
3-bromo-N-(1-methylbicyclo[2.2.1]hept-2-yl)propionamide;
N-((1R)-4-chloroindanyl)-3-bromopropionamide;
N-benzo[2,3-c]1,2,5-thiadiazol-4-yl-3-bromopropionamide;
3-bromo-N-indan-2-ylpropionamide;
3-bromo-N-indan-4-ylpropionamide;
N-((1S,2R)-2-hydroxyindanyl)-3-bromopropionamide;
3-bromo-N-indol-4-ylpropionamide;
N-((1S)-(1,2,3,4-tetrahydronaphthyl))-3-bromopropionamide;
3-bromo-N-(5-isoquinolyl)propionamide;
3-bromo-N-(6-quinolyl)propionamide;
3-bromo-N-(3-quinolyl)propionamide;
3-bromo-N-(5-quinolyl)propionamide;
3-bromo-N-(8-quinolyl)propionamide;
3-bromo-N-(2-quinolyl)propionamide;
1-acetyl-7-(3-bromo-2-oxopropyl)indoline;
3-bromo-N-chroman-4-ylpropionamide;
N-benzotriazolyl-3-bromopropionamide; and
3-bromo-N-[2-methyl-5-(methylethyl)cyclohexyl]propionamide.

E. Preparation of Compounds of Formula (1)

Similarly, following the procedure of 1A, 1B, or 1C above, but optionally replacing the amine with other amines of formula (10), and optionally replacing the acid halide with other compounds of formula (11), other compounds of formula (1) are prepared.

EXAMPLE 2

Preparation of a Compound of Formula (7)

A. Preparation of a Compound of Formula (7) in which $R^3$, $R^4$, $R^6$, $R^7$, $R^8$, $R^9$ and $R^{10}$ are Hydrogen and $R^5$ is Methyl

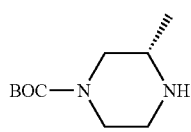

To a solution of 1-(tert-butoxycarbonyl)-2-tert-butyl-3-methyl-4-imidazolidinone (2 g, 8.3 mmol) (BOC-ON) in chloroform (15 ml) was added (2S)-2-methylpiperazine (5 g, 50 mmol), a compound of formula (6), and triethylamine (1.25 g, 12.5 mmol) in chloroform. The mixture was stirred for about 15 hours at room temperature, and then washed with water, the solvent removed from the organic layer under reduced pressure, and the residue purified using column chromatography, to give tert-butyl (3S)-3-methylpiperazinecarboxylate, a compound of formula (7).

B. Preparation of Compounds of Formula (7), varying $R^3$, $R^4$, $R^5$, $R^6$, $R^7$, $R^8$, $R^9$ and $R^{10}$ Similarly, following the procedure of Example 2A, replacing (2S)-2-methylpiperazine with other compounds of formula (6), other compounds of formula (7) are made.

EXAMPLE 3

Preparation of a Compound of Formula (9)

A. Preparation of a Compound of Formula (9) in which A and Z are $CH_2$, Q is Oxygen, $X^2$ is a Covalent Bond, $R^3$, $R^4$, $R^6$, $R^7$, $R^8$, $R^9$ and $R^{10}$ are Hydrogen and $R^5$ is Methyl, and $R^2$ is 2-Methylbenzothiazol-5-yl

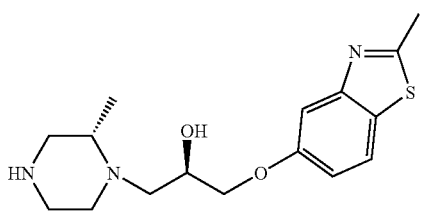

A solution of tert-butyl (3S)-3-methylpiperazinecarboxylate (3 g, 15 mmol) and 2-(2R)-methyl-5-(oxiran-2-ylmethoxy)benzothiazole, (3.3 g, 15 mmol), a compound of formula (5), was refluxed in ethanol for 24 hours. The solvent was removed under reduced pressure, and the residue was chromatographed on silica gel, eluting with methanol/dichloromethane 1/15, to yield tert-butyl (3S)-4-[(2S)-2-hydroxy-3-(2-methylbenzothiazol-5-yloxy)propyl]-3-methylpiperazinecarboxylate, a compound of formula (8).

A solution of tert-butyl (3S)-4-[(2R)-2-hydroxy-3-(2-methylbenzothiazol-5-yloxy)propyl]-3-methylpiperazinecarboxylate (3 g) in trifluoroacetic acid was stirred at room temperature for 3 days. The solvent was removed under reduced pressure, and the residue dissolved in 50 ml of methanol. The pH of this solution was adjusted to 8-9, the methanol removed under reduced pressure, and the residue, (2R)-1-((2S)-2-methylpiperazinyl)-3-(2-methylbenzothiazol-5-yloxy)propan-2-ol, a compound of formula (9), was used in the next reaction with no further purification.

B. Preparation of Other Compounds of Formula (9)

Similarly, following the procedure of 3A above, but optionally replacing tert-butyl (3S)-3-methylpiperazinecarboxylate with other compounds of formula (7), and optionally replacing 2-methyl-5-(oxiran-2-ylmethoxy)benzothiazole with other compounds of formula (5), the following compounds of formula (9) were prepared:

3-(2-methoxyphenoxy)-1-piperazinylpropan-2-ol;
3-(3-methoxyphenoxy)-1-piperazinylpropan-2-ol;
3-(4-methoxyphenoxy)-1-piperazinylpropan-2-ol;
3-(2-methylbenzothiazol-6-yloxy)-1-piperazinylpropan-2-ol;
3-(2-fluorophenoxy)-1-(3-methylpiperazinyl)propan-2-ol;
3-(2-phenylbenzothiazol-5-yloxy)-1-piperazinylpropan-2-ol;
3-(2-ethylbenzothiazol-5-yloxy)-1-piperazinylpropan-2-ol;

3-(2,5-dimethoxyphenoxy)-1-piperazinylpropan-2-ol;
3-(2-(4-chlorophenyl)benzoxazol-5-yloxy)-1-piperazinylpropan-2-ol;
3-(2-phenylbenzoxazol-5-yloxy)-1-piperazinylpropan-2-ol; and
3-(2-phenylbenzoxazol-6-yloxy)-1-piperazinylpropan-2-ol.

C. Preparation of Other Compounds of Formula (9)

Similarly, following the procedure of 3A above, but optionally replacing tert-butyl (3S)-3-methylpiperazinecarboxylate with other compounds of formula (7), and optionally replacing 2-methyl-5-(oxiran-2-ylmethoxy)benzothiazole with other compounds of formula (5), other compounds of formula (9) are prepared.

EXAMPLE 4

A. Preparation of a Compound of Formula I in which A, Y and Z are $CH_2$, Q and T are Oxygen, $X^1$ and $X^2$ are Covalent Bonds, $R^1$ and $R^2$ are 2-Methylbenzothiazol-5-yl, and $R^3$, $R^4$, $R^5$, $R^6$, $R^7$, $R^8$, and $R^{21}$ are Hydrogen

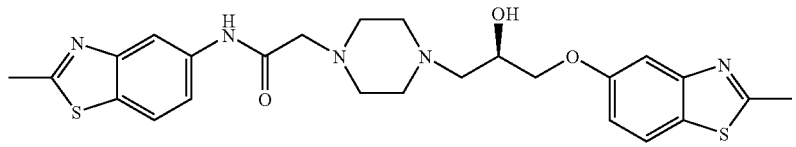

A mixture of (2R)-3-(2-methylbenzothiazol-5-yloxy)-1-piperazinylpropan-2-ol (0.2 g, 0.65 mmol) and 2-chloro-N-(2-methylbenzothiazol-5-yl)acetamide (0.155 g, 0.65 mmol) in ethanol was allowed to stir at reflux for 24 hours. The solvent was removed under reduced pressure and the residue was purified using preparative thin layer chromatography, to afford 2-{4-[(2R)-2-hydroxy-3-(2-methylbenzothiazol-5-yloxy)propyl]piperazinyl}-N-(2-methylbenzothiazol-5-yl) acetamide.

B. Alternative Preparation of a Compound of Formula I in which A, Y and Z are $CH_2$, Q and T are Oxygen, $X^1$ is —($CH_3$)CH—, $X^2$ is a Covalent Bond, $R^1$ is 2-Naphthyl $R^2$ is 2-Methylbenzothiazol-5-yl, and $R^3$, $R^4$, $R^5$, $R^6$, $R^7$, $R^8$, and $R^{21}$ are Hydrogen, by Resin Mediated Synthesis

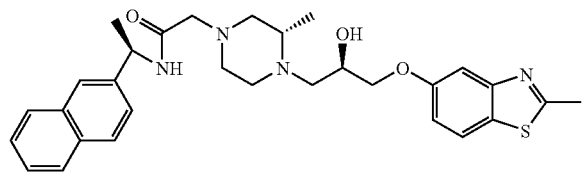

(2R)-1-((2S)-2-methylpiperazinyl)-3-(2-methylbenzothiazol-6-yloxy)propan-2-ol, a compound of formula (8), and N-((1R)-1-(2-naphthyl)ethyl)-2-chloroacetamide, a compound of formula (1), were dissolved in dichloroethane. A polystyrene-diisopropylethylamine (PS-DIEA) resin was added and the vial shaken at 80° C. overnight. After cooling to room temperature, 200 mg each of Polystyrene-Isocyanate resin were added and shaken at about room temperature overnight. After cooling to room temperature, contents of the vial were transferred into a frit fitted syringe, filtered, resins washed with dichloroethane repeatedly. After concentration by Speedvac™, the crude mixture was purified with semi-preparative HPLC (acetonitrile/water/0.1% TFA), fractions were analyzed by MS and HPLC. to provide N-((1R)-1-(2-naphthyl)ethyl)-2-{(3 S)-4-[(2R)-2-hydroxy-3-(2-methyl-benzothiazol-5-yloxy)propyl]-3-methylpiperazinyl}acetamide, a compound of Formula (I).

C. Preparation of a Compound of Formula I, varying A, Z, Q, $X^1$, $X^2$, T $R^1$, $R^2$, $R^3$, $R^4$, $R^5$, $R^6$, $R^7$, $R^8$ and $R^{21}$ Similarly, following the procedure of 3A or 3B above, the following compounds of Formula I were prepared:

N-benzothiazol-2-yl-2-{4-[2-hydroxy-3-(2-methoxyphenoxy)propyl]-piperazinyl}acetamide;

2-{4-[2-hydroxy-3-(2-methoxyphenoxy)propyl]piperazinyl}-N-(1-methylbenzimidazol-2-yl)acetamide;

N-(5-chlorobenzoxazol-2-yl)-2-{4-[2-hydroxy-3-(2-methoxyphenoxy)propyl]-piperazinyl}acetamide;

N-(4-chlorobenzoxazol-2-yl)-2-{4-[2-hydroxy-3-(2-methoxyphenoxy)propyl]piperazinyl}acetamide;

2-{4-[(2R)-2-hydroxy-3-(2-methylbenzothiazol-6-yloxy)propyl]piperazinyl}-N-(1-methylbenzimidazol-2-yl)acetamide;

2-{4-[(2R)-2-hydroxy-3-(2-methylbenzothiazol-6-yloxy)propyl]piperazinyl}-N-(4-chlorobenzothiazol-2-yl)acetamide;

2-{4-[(2R)-2-hydroxy-3-(2-methylbenzothiazol-6-yloxy)propyl]piperazinyl}-N-cyclohexylacetamide;

2-{4-[(2R)-2-hydroxy-3-(2-methylbenzothiazol-5-yloxy)propyl]piperazinyl}-N-cyclohexyl-N-methylacetamide;

2-{4-[(2R)-2-hydroxy-3-(2-methylbenzothiazol-6-yloxy)propyl]piperazinyl}-N-cyclopentylacetamide;

2-{4-[(2R)-2-methyl-3-(2-methylbenzothiazol-6-yloxy)propyl]piperazinyl}-N-(methylethyl)acetamide;

2-{4-[(2R)-2-hydroxy-3-(2-methylbenzothiazol-5-yloxy)propyl]piperazinyl}-N-bicyclo[2.2.1]hept-2-ylacetamide;

2-{4-[(2R)-2-hydroxy-3-(2-methoxyphenoxy)propyl]piperazinyl}-N-cyclohexylacetamide;

N-(4-chlorobenzothiazol-2-yl)-2-{4-[3-(2-fluorophenoxy)-2-hydroxypropyl]-2-methylpiperazinyl}acetamide;

N-cyclopentyl-2-{4-[3-(2-fluorophenoxy)-2-hydroxypropyl]-2-methylpiperazinyl}acetamide;

2-{4-[3-(2-fluorophenoxy)-2-hydroxypropyl]-3-methylpiperazinyl}-N-(5-methylisoxazol-3-yl)acetamide;

2-{4-[3-(2-fluorophenoxy)-2-hydroxypropyl]-3-methylpiperazinyl}-N-indan-5-ylacetamide;

2-{4-[3-(2-fluorophenoxy)-2-hydroxypropyl]-3-methylpiperazinyl}-N-naphth-1-ylacetamide;

N-(4-chloronaphth-1-yl)-2-{4-[3-(2-fluorophenoxy)-2-hydroxypropyl]-3-methylpiperazinyl}acetamide;

2-{4-[3-(2-fluorophenoxy)-2-hydroxypropyl]-3-methylpiperazinyl}-N-(2-pyrrolylphenyl)acetamide;

N-(5,6-dimethylbenzothiazol-2-yl)-2-{4-[3-(2-fluorophenoxy)-2-hydroxypropyl]-3-methylpiperazinyl}acetamide;

2-{4-[3-(2-fluorophenoxy)-2-hydroxypropyl]-3-methylpiperazinyl}-N-(8-quinolyl)acetamide;

2-{4-[3-(2-fluorophenoxy)-2-hydroxypropyl]-3-methylpiperazinyl}-N-(5-quinolyl)acetamide;

N-benzothiazol-2-yl-2-{4-[3-(2-fluorophenoxy)-2-hydroxypropyl]-3-methylpiperazinyl}acetamide;

N-(1H-indazol-5-yl)-2-{4-[3-(2-fluorophenoxy)-2-hydroxypropyl]-3-methylpiperazinyl}acetamide;

2-{4-[2-hydroxy-3-(2-methylbenzothiazol-5-yloxy)propyl]piperazinyl}-N-naphth-1-ylacetamide;

2-{4-[2-hydroxy-3-(4-methoxyphenyl)propyl]piperazinyl}-N-naphth-1ylacetamide;

2-{4-[2-hydroxy-3-(4-methoxyphenyl)propyl]piperazinyl}-N-naphth-1-ylacetamide;

2-{4-[2-hydroxy-3-(2-methylbenzothiazol-5-yloxy)propyl]piperazinyl}-N-indan-5-ylacetamide;

2-{4-[2-hydroxy-3-(4-methoxyphenyl)propyl]piperazinyl}-N-indan-5-ylacetamide;

2-{4-[3-(2-fluorophenoxy)-2-hydroxypropyl]piperazinyl}-N-indan-5-ylacetamide;

N-(1H-indazol-5-yl)-2-{4-[2-hydroxy-3-(2-methylbenzothiazol-5-yloxy)propyl]piperazinyl}acetamide;

N-(1H-indazol-5-yl)-2-{4-[2-hydroxy-3-(4-methoxyphenyl)propyl]-piperazinyl}acetamide;

N-(1H-indazol-5-yl)-2-{4-[3-(2-fluorophenoxy)-2-hydroxypropyl]piperazinyl}-acetamide;

N-benzothiazol-2-yl-2-{4-[2-hydroxy-3-(2-methylbenzothiazol-5-yloxy)propyl]-piperazinyl}acetamide;

N-benzothiazol-2-yl-2-{4-[2-hydroxy-3-(4-methoxyphenyl)propyl]-piperazinyl}acetamide;

N-benzothiazol-2-yl-2-{4-[3-(2-fluorophenoxy)-2-hydroxypropyl]-piperazinyl}acetamide;

N-cyclohexyl-2-{4-[2-hydroxy-3-(4-methoxyphenyl)propyl]piperazinyl}acetamide;

N-cyclohexyl-2-{4-[3-(2-fluorophenoxy)-2-hydroxypropyl]piperazinyl}acetamide;

N-cyclopentyl-2-{4-[3-(2-fluorophenoxy)-2-hydroxypropyl]piperazinyl}acetamide;

2-{4-[2-hydroxy-3-(2-methoxyphenoxy)propyl]piperazinyl}-N-naphth-1-ylacetamide;

2-{4-[2-hydroxy-3-(2-methoxyphenoxy)propyl]piperazinyl}-N-indan-5-ylacetamide;

N-(1H-indazol-5-yl)-2-{4-[2-hydroxy-3-(2-methoxyphenoxy)propyl]-piperazinyl}acetamide;

N-cyclopentyl-2-{4-[2-hydroxy-3-(2-methoxyphenoxy)propyl]piperazinyl}acetamide;

N-(1H-indazol-5-yl)-2-{4-[2-hydroxy-3-(2-phenylbenzothiazol-5-yloxy)propyl]-piperazinyl}acetamide;

N-cyclohexyl-2-{4-[2-hydroxy-3-(2-phenylbenzothiazol-5-yloxy)propyl]-piperazinyl}acetamide;

N-cyclopentyl-2-{4-[2-hydroxy-3-(2-phenylbenzothiazol-5-yloxy)propyl]-piperazinyl}acetamide;

N-cyclopentyl-2-{4-[3-(2-ethylbenzothiazol-5-yloxy)-2-hydroxypropyl]-piperazinyl}acetamide;

N-cyclohexyl-2-{4-[3-(2-ethylbenzothiazol-5-yloxy)-2-hydroxypropyl]-piperazinyl}acetamide;

N-benzothiazol-2-yl-2-{4-[3-(2-ethylbenzothiazol-5-yloxy)-2-hydroxypropyl]-piperazinyl}acetamide;

N-(1H-indazol-5-yl)-2-{4-[3-(2-ethylbenzothiazol-5-yloxy)-2-hydroxypropyl]-piperazinyl}acetamide;

2-{4-[3-(2-ethylbenzothiazol-5-yloxy)-2-hydroxypropyl]piperazinyl}-N-indan-5-ylacetamide;

2-{4-[3-(2-ethylbenzothiazol-5-yloxy)-2-hydroxypropyl]piperazinyl}-N-naphth-1-ylacetamide;

2-{4-[3-(2,5-dimethoxyphenoxy)-2-hydroxypropyl]piperazinyl}-N-cyclopentylacetamide;

2-{4-[3-(2,5-dimethoxyphenoxy)-2-hydroxypropyl]piperazinyl}-N-naphth-1-ylacetamide;

N-cyclopentyl-2-(4-{3-[(2-fluorophenyl)carbonylamino]-2-hydroxypropyl}-piperazinyl)acetamide;

2-{4-[3-(2,5-dimethoxyphenoxy)-2-hydroxypropyl]piperazinyl}-N-indan-5-ylacetamide;

2-{4-[3-(2,5-dimethoxyphenoxy)-2-hydroxypropyl]piperazinyl}-N-benzylacetamide;

2-{4-[3-(2,5-dimethoxyphenoxy)-2-hydroxypropyl]piperazinyl}-N-cyclohexylacetamide;

2-{4-[(2R)-2-hydroxy-3-(2-methylbenzothiazol-5-yloxy)propyl]piperazinyl}-N-adamantanylacetamide;

2-{4-[(2R)-2-hydroxy-3-(2-methylbenzothiazol-5-yloxy)propyl]piperazinyl}-N-adamantan-2-ylacetamide;

2-{4-[(2R)-2-hydroxy-3-(2-methylbenzothiazol-5-yloxy)propyl]piperazinyl}-N-(5,6,7,8-tetrahydronaphthyl)acetamide;

2-(4-{(2R)-3-[2-(4-chlorophenyl)benzoxazol-5-yloxy]-2-hydroxypropyl}piperazinyl)-N-adamantanylacetamide;

2-{4-[(2R)-2-hydroxy-3-(2-methylbenzothiazol-5-yloxy)propyl]piperazinyl}-N-((2S,1R)-2-hydroxyindanyl)acetamide;

2-{4-[(2R)-2-hydroxy-3-(2-methylbenzothiazol-5-yloxy)propyl]piperazinyl}-N-((1S)indanyl)acetamide;

N-(2H,3H-benzo[e]1,4-dioxin-6-yl)-2-{4-[(2R)-2-hydroxy-3-(2-methylbenzothiazol-5-yloxy)propyl]piperazinyl}acetamide;

2-{4-[(2R)-2-hydroxy-3-(2-methylbenzothiazol-5-yloxy)propyl]piperazinyl}-N-((1S)indanyl)acetamide;

N-((1R,2R)-2-hydroxyindanyl)-2-{4-[(2R)-2-hydroxy-3-(2-phenylbenzoxazol-5-yloxy)propyl]piperazinyl}acetamide;

N-((1R)(1,2,3,4-tetrahydronaphthyl))-2-{4-[(2R)-2-hydroxy-3-(2-phenylbenzoxazol-6-yloxy)propyl]piperazinyl}acetamide;

2-{4-[(2R)-2-hydroxy-3-(2-phenylbenzoxazol-5-yloxy)propyl]piperazinyl}-N-indan-5-ylacetamide;

N-((1R)(1,2,3,4-tetrahydronaphthyl))-2-{4-[(2R)-2-hydroxy-3-(2-phenylbenzoxazol-5-yloxy)propyl]piperazinyl}acetamide;

N-((1R)indanyl)-2-{4-[(2R)-2-hydroxy-3-(2-phenylbenzoxazol-5-yloxy)propyl]-piperazinyl}acetamide;

2-{4-[(2R)-2-hydroxy-3-(2-phenylbenzoxazol-5-yloxy)propyl]piperazinyl}-N-benzotriazolylacetamide;

2-{4-[(2R)-2-hydroxy-3-(2-phenylbenzoxazol-5-yloxy)propyl]piperazinyl}-indol-4-ylacetamide;

2-{4-[(2R)-2-hydroxy-3-(2-phenylbenzoxazol-6-yloxy)propyl]piperazinyl}-N-((2S,1R)-2-hydroxyindanyl)acetamide;

2-{4-[(2R)-2-hydroxy-3-(2-phenylbenzoxazol-5-yloxy)propyl]piperazinyl}-N-((1S)indanyl)acetamide;

N-((1S)-4-chloroindanyl)-2-{4-[(2R)-2-hydroxy-3-(2-phenylbenzoxazol-5-yloxy)propyl]piperazinyl}acetamide;

2-{4-[(2R)-2-hydroxy-3-(2-phenylbenzoxazol-5-yloxy)propyl]piperazinyl}-N-(5,6,7,8-tetrahydronaphthyl)acetamide;

2-{4-[(2R)-2-hydroxy-3-(2-phenylbenzoxazol-5-yloxy)propyl]piperazinyl}-N-indan-2-ylacetamide;

2-{4-[(2R)-2-hydroxy-3-(2-phenylbenzoxazol-5-yloxy)propyl]piperazinyl}-N-indan-4-ylacetamide;

2-{4-[(2R)-2-hydroxy-3-(2-methylbenzothiazol-5-yloxy)propyl]piperazinyl}-N-indan-4-ylacetamide;

N-((1R)(1,2,3,4-tetrahydronaphthyl))-2-{4-[(2R)-2-hydroxy-3-(2-methylbenzothiazol-5-yloxy)propyl]piperazinyl}acetamide;

2-{4-[(2R)-2-hydroxy-3-(2-methylbenzothiazol-5-yloxy)propyl]piperazinyl}-N-indan-2-ylacetamide;

2-{4-[(2R)-2-hydroxy-3-(2-methylbenzothiazol-5-yloxy) propyl]piperazinyl}-N-((1S,2R)-2-hydroxyindanyl)acetamide;

2-{4-[(2R)-2-hydroxy-3-(2-methylbenzothiazol-5-yloxy) propyl]piperazinyl}-N-((1S,2R)-4-fluoro-2-hydroxyindanyl)acetamide;

2-{4-[(2R)-2-hydroxy-3-(2-phenylbenzoxazol-5-yloxy) propyl]piperazinyl}-N-(5-quinolyl)acetamide;

2-{4-[(2R)-2-hydroxy-3-(2-phenylbenzoxazol-5-yloxy) propyl]piperazinyl}-N-(6-quinolyl)acetamide;

2-{4-[(2R)-2-hydroxy-3-(2-methylbenzothiazol-5-yloxy) propyl]piperazinyl}-N-(3-quinolyl)acetamide;

2-{4-[(2R)-2-hydroxy-3-(2-methylbenzothiazol-5-yloxy) propyl]piperazinyl}-N-(5-quinolyl)acetamide;

2-{4-[(2R)-2-hydroxy-3-(2-methylbenzothiazol-5-yloxy) propyl]piperazinyl}-N-(8-quinolyl)acetamide;

2-{4-[(2R)-2-hydroxy-3-(2-phenylbenzoxazol-5-yloxy) propyl]piperazinyl}-N-(7-quinolyl)acetamide;

2-{4-[(2R)-2-hydroxy-3-(2-phenylbenzoxazol-5-yloxy) propyl]piperazinyl}-N-(3-quinolyl)acetamide;

2-{4-[(2R)-2-hydroxy-3-(2-phenylbenzoxazol-5-yloxy) propyl]piperazinyl}-N-(1-acetylindolin-7-yl)acetamide;

2-{4-[(2R)-2-hydroxy-3-(2-phenylbenzoxazol-5-yloxy) propyl]piperazinyl}-N-chroman-4-ylacetamide;

2-{4-[(2R)-2-hydroxy-3-(2-methylbenzothiazol-5-yloxy) propyl]piperazinyl}-N-chroman-4-ylacetamide;

2-{4-[(2R)-2-hydroxy-3-(2-methylbenzothiazol-5-yloxy) propyl]piperazinyl}-N-benzotriazolylacetamide;

2-{4-[(2R)-2-hydroxy-3-(2-phenylbenzoxazol-5-yloxy) propyl]piperazinyl}-N-(2,6,6-trimethylbicyclo[3.1.1]hept-3-yl)acetamide;

N-((1R)-1-(2-naphthyl)ethyl)-2-{4-[(2R)-2-hydroxy-3-(2-phenylbenzoxazol-5-yloxy)propyl]piperazinyl}acetamide;

2-{4-[(2R)-2-hydroxy-3-(2-methylbenzothiazol-5-yloxy) propyl]piperazinyl}-N-((5S,3R)-2,6,6-trimethylbicyclo[3.1.1]hept-3-yl)acetamide;

2-{4-[(2R)-2-hydroxy-3-(2-methylbenzothiazol-5-yloxy) propyl]piperazinyl}-N-(2,6,6-trimethylbicyclo[3.1.1]hept-3-yl)acetamide;

2-{4-[(2R)-2-hydroxy-3-(2-methylbenzothiazol-5-yloxy) propyl]piperazinyl}-N-[(2,6-difluorophenyl)methyl]acetamide;

2-{4-[(2R)-2-hydroxy-3-(2-methylbenzothiazol-5-yloxy) propyl]piperazinyl}-N-benzylacetamide;

2-{4-[(2R)-2-hydroxy-3-(2-methylbenzothiazol-5-yloxy) propyl]piperazinyl}-N-(cyclohexylmethyl)acetamide;

2-{4-[(2R)-2-hydroxy-3-(2-methoxyphenoxy)propyl]piperazinyl}-N-benzylacetamide;

N-(2,2-dimethylpropyl)-2-{4-[3-(2-fluorophenoxy)-2-hydroxypropyl]-3-methylpiperazinyl}acetamide;

N-(2,2-diphenylethyl)-2-{4-[3-(2-fluorophenoxy)-2-hydroxypropyl]-3-methylpiperazinyl}acetamide;

N-[2-(3,4-dimethoxyphenyl)ethyl]-2-{4-[3-(2-fluorophenoxy)-2-hydroxypropyl]-3-methylpiperazinyl}acetamide;

2-{4-[3-(2-fluorophenoxy)-2-hydroxypropyl]-3-methylpiperazinyl}-N-[3-(methylphenylamino)propyl]acetamide;

2-{4-[(2R)-3-(2-fluorophenoxy)-2-hydroxypropyl](3S)-3-methylpiperazinyl}-N-[(2,4-dichlorophenyl)methyl]acetamide;

2-{4-[(2R)-3-(2-fluorophenoxy)-2-hydroxypropyl](3S)-3-methylpiperazinyl}-N-[(3,4-dichlorophenyl)methyl]acetamide;

2-{4-[(2R)-3-(2-fluorophenoxy)-2-hydroxypropyl](3S)-3-methylpiperazinyl}-N-[(4-chlorophenyl)methyl]acetamide;

2-{4-[(2R)-3-(2-fluorophenoxy)-2-hydroxypropyl](3S)-3-methylpiperazinyl}-N-[(3,5-difluorophenyl)methyl]acetamide;

2-{4-[(2R)-3-(2-fluorophenoxy)-2-hydroxypropyl](3S)-3-methylpiperazinyl}-N-[(3-fluorophenyl)methyl]acetamide;

2-{4-[(2R)-3-(2-fluorophenoxy)-2-hydroxypropyl](3S)-3-methylpiperazinyl}-N-[(2-fluorophenyl)methyl]acetamide;

2-{4-[(2R)-3-(2-fluorophenoxy)-2-hydroxypropyl](3S)-3-methylpiperazinyl}-N-[(2,4-difluorophenyl)methyl]acetamide;

2-{4-[(2R)-3-(2-fluorophenoxy)-2-hydroxypropyl](3S)-3-methylpiperazinyl}-N-[(2,6-difluorophenyl)methyl]acetamide;

2-{4-[(2R)-3-(2-fluorophenoxy)-2-hydroxypropyl](3S)-3-methylpiperazinyl}-N-[(2,5-difluorophenyl)methyl]acetamide;

2-{4-[(2R)-3-(2-fluorophenoxy)-2-hydroxypropyl](3S)-3-methylpiperazinyl}-N-[(3,4-difluorophenyl)methyl]acetamide;

2-{4-[(2R)-3-(2-fluorophenoxy)-2-hydroxypropyl](3S)-3-methylpiperazinyl}-N-[(3-chlorophenyl)methyl]acetamide;

2-{4-[(2R)-3-(2-fluorophenoxy)-2-hydroxypropyl](3S)-3-methylpiperazinyl}-N-[(2-methylphenyl)methyl]acetamide;

2-{4-[(2R)-3-(2-fluorophenoxy)-2-hydroxypropyl](3S)-3-methylpiperazinyl}-N-[(3-methylphenyl)methyl]acetamide;

2-{4-[(2R)-3-(2-fluorophenoxy)-2-hydroxypropyl](3S)-3-methylpiperazinyl}-N-[(4-methylphenyl)methyl]acetamide;

N-[(4-chlorophenyl)methyl]-2-{4-[2-hydroxy-3-(2-methylbenzothiazol-5-yloxy)propyl]piperazinyl}acetamide;

N-[(4-chlorophenyl)methyl]-2-{4-[2-hydroxy-3-(2-methylbenzothiazol-5-yloxy)propyl]piperazinyl}acetamide;

N-[(4-chlorophenyl)methyl]-2-{4-[2-hydroxy-3-(4-methoxyphenyl)propyl]-piperazinyl}acetamide;

N-[(3,4-dichlorophenyl)methyl]-2-{4-[2-hydroxy-3-(2-methylbenzothiazol-5-yloxy)propyl]piperazinyl}acetamide;

N-[(3,4-dichlorophenyl)methyl]-2-{4-[2-hydroxy-3-(4-methoxyphenyl)propyl]-piperazinyl}acetamide;

N-[(3,4-dichlorophenyl)methyl]-2-{4-[3-(2-fluorophenoxy)-2-hydroxypropyl]-piperazinyl}acetamide;

N-[(2,4-dichlorophenyl)methyl]-2-{4-[2-hydroxy-3-(2-methylbenzothiazol-5-yloxy)propyl]piperazinyl}acetamide;

N-[(2,4-dichlorophenyl)methyl]-2-{4-[2-hydroxy-3-(4-methoxyphenyl)propyl]-piperazinyl}acetamide;

N-[(2,4-dichlorophenyl)methyl]-2-{4-[3-(2-fluorophenoxy)-2-hydroxypropyl]-piperazinyl}acetamide;

2-{4-[2-hydroxy-3-(4-methoxyphenyl)propyl]piperazinyl}-N-benzylacetamide;

2-{4-[3-(2-fluorophenoxy)-2-hydroxypropyl]piperazinyl}-N-benzylacetamide;

2-{4-[2-hydroxy-3-(2-methoxyphenoxy)propyl]piperazinyl}-N-benzylacetamide;

2-{4-[3-(2-fluorophenoxy)-2-hydroxypropyl]piperazinyl}-N-(2-phenylethyl)acetamide;

2-{4-[2-hydroxy-3-(2-methoxyphenoxy)propyl]piperazinyl}-N-(2-phenylethyl)acetamide;

N-[2-(2,4-dichlorophenyl)ethyl]-2-{4-[2-hydroxy-3-(2-methoxyphenoxy)propyl]-piperazinyl}acetamide;

N-[(4-chlorophenyl)methyl]-2-[4-(2-hydroxy-2-phenylethyl)piperazinyl]acetamide;

2-{4-[2-hydroxy-3-(2-methylbenzothiazol-5-yloxy)propyl]piperazinyl}-N-(2-phenylethyl)acetamide;

N-[2-(2,4-dichlorophenyl)ethyl]-2-{4-[2-hydroxy-3-(2-methylbenzothiazol-5-yloxy)propyl]piperazinyl}acetamide;

N-[2-(2,4-dichlorophenyl)ethyl]-2-{4-[3-(2-fluorophenoxy)-2-hydroxypropyl]-piperazinyl}acetamide;

2-{4-[3-(2-ethylbenzothiazol-5-yloxy)-2-hydroxypropyl]piperazinyl}-N-(2-phenylethyl)acetamide;

2-{4-[3-(2-ethylbenzothiazol-5-yloxy)-2-hydroxypropyl]piperazinyl}-N-benzylacetamide;

N-[(2,4-dichlorophenyl)methyl]-2-{4-[3-(2-ethylbenzothiazol-5-yloxy)-2-hydroxypropyl]piperazinyl}acetamide;

N-[(3,4-dichlorophenyl)methyl]-2-{4-[3-(2-ethylbenzothiazol-5-yloxy)-2-hydroxypropyl]piperazinyl}acetamide;

N-[(4-chlorophenyl)methyl]-2-{4-[3-(2-ethylbenzothiazol-5-yloxy)-2-hydroxypropyl]piperazinyl}acetamide;

N-[2-(2,4-dichlorophenyl)ethyl]-2-{4-[2-hydroxy-3-(2-phenylbenzothiazol-5-yloxy)propyl]piperazinyl}acetamide;

N-[(3,4-dichlorophenyl)methyl]-2-{4-[3-(2,5-dimethoxyphenoxy)-2-hydroxypropyl]piperazinyl}acetamide;

N-[(2,4-dichlorophenyl)methyl]-2-{4-[3-(2,5-dimethoxyphenoxy)-2-hydroxypropyl]-piperazinyl}acetamide;

2-{4-[3-(2,5-dimethoxyphenoxy)-2-hydroxypropyl]piperazinyl}-N-benzylacetamide;

2-{4-[3-(2,5-dimethoxyphenoxy)-2-hydroxypropyl]piperazinyl}-N-(2-phenylethyl)acetamide;

N-[2-(2,4-dichlorophenyl)ethyl]-2-{4-[3-(2,5-dimethoxyphenoxy)-2-hydroxypropyl]piperazinyl}acetamide;

N-((1R)-1-phenylethyl)-2-{4-[(2R)-2-hydroxy-3-(2-methylbenzothiazol-5-yloxy)propyl]piperazinyl}acetamide;

2-{4-[(2R)-2-hydroxy-3-(2-methylbenzothiazol-5-yloxy)propyl]piperazinyl}-N-((1S)-1-phenylethyl)acetamide;

2-{4-[(2R)-2-hydroxy-3-(2-phenylbenzoxazol-5-yloxy)propyl]piperazinyl}-N-((1S)-1-phenylethyl)acetamide;

N-((1R)-1-phenylethyl)-2-{4-[(2R)-2-hydroxy-3-(2-methylbenzothiazol-5-yloxy)propyl]piperazinyl}acetamide;

N-((1R)-1-naphthylethyl)-2-{4-[(2R)-2-hydroxy-3-(2-phenylbenzoxazol-5-yloxy)propyl]piperazinyl}acetamide;

N-((1S)-1-(2-naphthyl)ethyl)-2-{4-[(2R)-2-hydroxy-3-(2-phenylbenzoxazol-5-yloxy)propyl]piperazinyl}acetamide;

2-{4-[(2R)-2-hydroxy-3-(2-phenylbenzoxazol-5-yloxy)propyl]piperazinyl}-N-((1S)-1-naphthylethyl)acetamide;

N-[(1R)-1-(4-fluorophenyl)ethyl]-2-{4-[(2R)-2-hydroxy-3-(2-phenylbenzoxazol-5-yloxy)propyl]piperazinyl}acetamide;

N-[(1S)-1-(4-fluorophenyl)ethyl]-2-{4-[(2R)-2-hydroxy-3-(2-phenylbenzoxazol-5-yloxy)propyl]piperazinyl}acetamide;

N-((1S)-1-(2-naphthyl)ethyl)-2-{4-[(2R)-2-hydroxy-3-(2-methylbenzothiazol-5-yloxy)propyl]piperazinyl}acetamide;

2-{4-[(2R)-2-hydroxy-3-(2-methylbenzothiazol-5-yloxy)propyl]piperazinyl}-N-((1S)-1-naphthylethyl)acetamide;

2-{4-[(2R)-2-hydroxy-3-(2-methylbenzothiazol-5-yloxy)propyl]piperazinyl}-N-((1S)-1-naphthylethyl)acetamide;

N-[(1S)-1-(4-fluorophenyl)ethyl]-2-{4-[(2R)-2-hydroxy-3-(2-methylbenzothiazol-5-yloxy)propyl]piperazinyl}acetamide;

N-[(1R)-1-(4-fluorophenyl)ethyl]-2-{4-[(2R)-2-hydroxy-3-(2-methylbenzothiazol-5-yloxy)propyl]piperazinyl}acetamide;

N-((1R)-1-(2-naphthyl)ethyl)-2-{4-[(2R)-2-hydroxy-3-(2-methylbenzothiazol-5-yloxy)propyl]piperazinyl}acetamide;

methyl (2R)-2-(2-{4-[(2R)-2-hydroxy-3-(2-methylbenzothiazol-5-yloxy)propyl]-piperazinyl}acetylamino)-2-phenylacetate;

ethyl (2S)-2-(3-{4-[(2R)-2-hydroxy-3-(2-methylbenzothiazol-6-yloxy)propyl]-piperazinyl}propanoylamino)-2-[4-(trifluoromethyl)phenyl]acetate;

ethyl 2-(2-{4-[(2R)-2-hydroxy-3-(2-methylbenzothiazol-5-yloxy)propyl]-piperazinyl}acetylamino)(2S)-2-(4-fluorophenyl)acetate;

2-(2-{4-[(2R)-2-hydroxy-3-(2-methylbenzothiazol-5-yloxy)propyl]-piperazinyl}acetylamino)(2S)-2-(4-fluorophenyl)acetic acid;

methyl 2-(2-{4-[(2R)-2-hydroxy-3-(2-methylbenzothiazol-5-yloxy)propyl]-piperazinyl}acetylamino)(2S)-2-cyclohexylacetate;

2-(2-{4-[(2R)-2-hydroxy-3-(2-methylbenzothiazol-5-yloxy)propyl]piperazinyl}-acetylamino)(2S)-2-phenylacetic acid;

2-(2-{4-[(2R)-2-hydroxy-3-(2-methylbenzothiazol-5-yloxy)propyl]-piperazinyl}acetylamino)(2S)-2-[4-(trifluoromethyl)phenyl]acetic acid;

2-{4-[(2R)-2-hydroxy-3-(2-methylbenzothiazol-5-yloxy)propyl]piperazinyl}-N-((1S)-2-hydroxy-1-phenylethyl)acetamide;

2-{4-[(2R)-2-hydroxy-3-(2-methylbenzothiazol-5-yloxy)propyl]piperazinyl}-N-((1S)-2-hydroxy-1-phenylethyl)acetamide;

N-((1R)-2-hydroxy-1-phenylethyl)-2-{4-[(2R)-2-hydroxy-3-(2-methylbenzothiazol-5-yloxy)propyl]piperazinyl}acetamide;

N-((1S)(1,2,3-tetrahydronaphthyl))-2-{4-[(2R)-2-hydroxy-3-(2-methylbenzothiazol-5-yloxy)propyl]piperazinyl}acetamide;

N-((1R)(1,2,3-tetrahydronaphthyl))-2-{4-[(2R)-2-hydroxy-3-(2-methylbenzothiazol-5-yloxy)propyl]piperazinyl}acetamide;

2-{4-[(2R)-2-hydroxy-3-(2-methylbenzothiazol-5-yloxy)propyl]piperazinyl}-N-indanylacetamide;

2-{4-[(2R)-2-hydroxy-3-(2-methylbenzothiazol-5-yloxy)propyl]piperazinyl}-N-indan-4-ylacetamide;

2-{4-[(2R)-2-hydroxy-3-(2-methylbenzothiazol-5-yloxy)propyl]piperazinyl}-N-indol-4-ylacetamide;

2-{4-[(2R)-2-hydroxy-3-(2-methylbenzothiazol-5-yloxy)propyl]piperazinyl}-N-((5S,3R)-2,6,6-trimethylbicyclo[3.1.1]hept-3-yl)acetamide;

2-{4-[(2R)-2-hydroxy-3-(2-methylbenzothiazol-5-yloxy)propyl]piperazinyl}-N-((2S,1R)-2-hydroxy-1-methyl-2-phenylethyl)acetamide;

2-{4-[(2R)-2-hydroxy-3-(2-methylbenzothiazol-5-yloxy)propyl]piperazinyl}-N-((1S,2R)-2-hydroxy-1-methyl-2-phenylethyl)acetamide;

2-{4-[(2R)-2-hydroxy-3-(2-methylbenzothiazol-5-yloxy)propyl]piperazinyl}-N-(5-quinolyl)acetamide;

2-{4-[(2R)-2-hydroxy-3-(2-methylbenzothiazol-5-yloxy)propyl]piperazinyl}-N-(6-quinolyl)acetamide;

2-{4-[(2R)-2-hydroxy-3-(2-methylbenzothiazol-5-yloxy)propyl]piperazinyl}-N-(3-quinolyl)acetamide;

2-{4-[(2R)-2-hydroxy-3-(2-methylbenzothiazol-5-yloxy)propyl]piperazinyl}-N-(8-quinolyl)acetamide;

2-{4-[(2R)-2-hydroxy-3-(2-methylbenzothiazol-5-yloxy)propyl]piperazinyl}-N-(2-methyl(4-quinolyl))acetamide;

N-((1R)-2-hydroxy-1-phenylethyl)-2-{4-[(2R)-2-hydroxy-3-(2-methylbenzothiazol-5-yloxy)propyl]piperazinyl}acetamide;

2-{4-[(2R)-2-hydroxy-3-(2-methylbenzothiazol-5-yloxy)propyl]piperazinyl}-N-((1S)-2-hydroxy-1-phenylethyl)acetamide;

2-{4-[(2R)-2-hydroxy-3-(2-methylbenzothiazol-5-yloxy) propyl]piperazinyl}-N-(1-acetylindolin-7-yl)acetamide;

2-{4-[(2R)-2-hydroxy-3-(2-methylbenzothiazol-5-yloxy) propyl]piperazinyl}-N-chroman-4-ylacetamide;

2-{4-[(2R)-2-hydroxy-3-(2-methylbenzothiazol-5-yloxy) propyl]piperazinyl}-N-(9-ethylcarbazol-3-yl)acetamide;

2-{4-[(2R)-2-hydroxy-3-(2-methylbenzothiazol-5-yloxy) propyl]piperazinyl}-N-((1S)-1-naphthylethyl)acetamide;

N-((1R)-1-naphthylethyl)-2-{4-[(2R)-2-hydroxy-3-(2-methylbenzothiazol-5-yloxy)propyl]piperazinyl}acetamide;

N-((1R)-1-naphthylethyl)-2-{4-[(2R)-2-hydroxy-3-(2-methylbenzothiazol-5-yloxy)propyl]piperazinyl}acetamide;

N-((1S)-1-(2-naphthyl)ethyl)-2-{4-[(2R)-2-hydroxy-3-(2-methylbenzothiazol-5-yloxy)propyl]piperazinyl}acetamide;

N-[(1S)-1-(4-fluorophenyl)ethyl]-2-{4-[(2R)-2-hydroxy-3-(2-methylbenzothiazol-5-yloxy)propyl]piperazinyl}acetamide;

N-[(1R)-1-(4-fluorophenyl)ethyl]-2-{4-[(2R)-2-hydroxy-3-(2-methylbenzothiazol-5-yloxy)propyl]piperazinyl}acetamide;

2-{4-[(2R)-2-hydroxy-3-(2-phenylbenzoxazol-5-yloxy) propyl]piperazinyl}-N-((1S)-1-phenylethyl)acetamide;

N-[(1R)-1-phenylethyl]-2-{4-[(2R)-2-hydroxy-3-(2-methylbenzothiazol-5-yloxy)propyl]piperazinyl}acetamide;

2-{4-[(2R)-2-hydroxy-3-(2-phenylbenzoxazol-5-yloxy) propyl]piperazinyl}-N-(4-fluoro(5,6,7,8-tetrahydronaphthyl))acetamide;

N-((1S)(1,2,3,4-tetrahydronaphthyl))-2-{4-[(2R)-2-hydroxy-3-(2-phenylbenzoxazol-5-yloxy)propyl]piperazinyl}acetamide;

N-((1R)(1,2,3,4-tetrahydronaphthyl))-2-{4-[(2R)-2-hydroxy-3-(2-phenylbenzoxazol-5-yloxy)propyl]piperazinyl}acetamide;

N-(1S)-indanyl-2-{4-[(2R)-2-hydroxy-3-(2-phenylbenzoxazol-5-yloxy)propyl]-piperazinyl}acetamide;

N-((1R)indanyl)-2-{4-[(2R)-2-hydroxy-3-(2-phenylbenzoxazol-5-yloxy)propyl]-piperazinyl}acetamide;

2-{4-[(2R)-2-hydroxy-3-(2-phenylbenzoxazol-5-yloxy) propyl]piperazinyl}-N-indan-2-ylacetamide;

2-{4-[(2R)-2-hydroxy-3-(2-phenylbenzoxazol-5-yloxy) propyl]piperazinyl}-N-indan-5-ylacetamide;

2-{4-[(2R)-2-hydroxy-3-(2-phenylbenzoxazol-5-yloxy) propyl]piperazinyl}-N-indan-4-ylacetamide;

2-{4-[(2R)-2-hydroxy-3-(2-phenylbenzoxazol-5-yloxy) propyl]piperazinyl}-N-((1S,2S)-2-hydroxyindanyl)acetamide;

N-((1R,2R)-2-hydroxyindanyl)-2-{4-[(2R)-2-hydroxy-3-(2-phenylbenzoxazol-5-yloxy)propyl]piperazinyl}acetamide;

2-{4-[(2R)-2-hydroxy-3-(2-phenylbenzoxazol-5-yloxy) propyl]piperazinyl}-N-indol-4-ylacetamide;

N-(2H,3H-benzo[e]1,4-dioxin-5-yl)-2-{4-[(2R)-2-hydroxy-3-(2-phenylbenzoxazol-5-yloxy)propyl]piperazinyl}acetamide;

2-{4-[(2R)-2-hydroxy-3-(2-phenylbenzoxazol-5-yloxy) propyl]piperazinyl}-N-(2,6,6-trimethylbicyclo[3.1.1]hept-3-yl)acetamide;

2-{4-[(2R)-2-hydroxy-3-(2-phenylbenzoxazol-5-yloxy) propyl]piperazinyl}-N-(5-quinolyl)acetamide;

2-{4-[(2R)-2-hydroxy-3-(2-phenylbenzoxazol-5-yloxy) propyl]piperazinyl}-N-(7-quinolyl)acetamide;

2-{4-[(2R)-2-hydroxy-3-(2-phenylbenzoxazol-5-yloxy) propyl]piperazinyl}-N-(3-quinolyl)acetamide;

2-{4-[(2R)-2-hydroxy-3-(2-phenylbenzoxazol-5-yloxy) propyl]piperazinyl}-N-chroman-4-ylacetamide;

2-{4-[(2R)-2-hydroxy-3-(2-phenylbenzoxazol-5-yloxy) propyl]piperazinyl}-N-((1S)-1-naphthylethyl)acetamide;

N-((1R)-1-naphthylethyl)-2-{4-[(2R)-2-hydroxy-3-(2-phenylbenzoxazol-5-yloxy)propyl]-piperazinyl}acetamide;

N-((1R)-1-(2-naphthyl)ethyl)-2-{4-[(2R)-2-hydroxy-3-(2-phenylbenzoxazol-5-yloxy)propyl] piperazinyl}acetamide;

2-{4-[2-hydroxy-3-(2-methoxyphenoxy)propyl]piperazinyl}-N-(2-methylbenzothiazol-5-yl)acetamide;

N-benzothiazol-2-yl-2-{4-[2-hydroxy-3-(2-methoxyphenoxy)propyl]piperazinyl}-acetamide;

2-{(3S)-4-[(2R)-2-hydroxy-3-(2-methylbenzothiazol-5-yloxy)propyl]-3-methylpiperazinyl}-N-(5-phenyl(1,3,4-thiadiazol-2-yl))acetamide;

2-{(3S)-4-[(2R)-2-hydroxy-3-(2-methylbenzothiazol-5-yloxy)propyl]-3-methylpiperazinyl}-N-[2-(4-chlorophenyl)(1,3-thiazol-4-yl)]acetamide;

N-((1S)-1-(2-naphthyl)ethyl)-2-{4-[(2R)-2-hydroxy-3-(2-phenylbenzoxazol-5-yloxy)propyl] piperazinyl}acetamide; and N-[(1S)-1-(4-fluorophenyl)ethyl]-2-{4-[(2R)-2-hydroxy-3-(2-phenylbenzoxazol-5-yloxy)propyl] piperazinyl}acetamide.

D. Preparation of a Compound of Formula I, varing A, Z, Q, $X^1$, $X^2$, T $R^1$, $R^2$, $R^3$, $R^4$, $R^5$, $R^6$, $R^7$, $R^8$, and $R^{21}$ Similarly, following the procedure of 3A or 3B above, other compounds of Formula I are prepared:

All compounds of Formula I provided satisfactory NMR and Mass Spectrometry characterization data.

EXAMPLE 5

Preparation of a Compound of Formula I in which A is $CH_2$, $R^1$ is 2,6-Dimethylphenyl, $R^2$ is 2-Methylbenzothiazol-5-yl, $R^3$, $R^4$, $R^5$, $R^6$, $R^7$, $R^8$, and $R^{21}$ are Hydrogen, T is Oxygen, $X^1$ is a Covalent Bond, and Y is —$CH_2CH_2$—

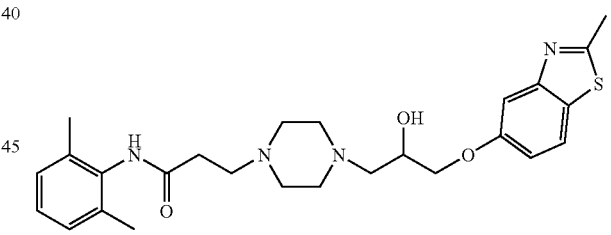

A. Preparation of a Compound of Formula I

Step 1—Preparation of a Compound of Formula (3)

To a mixture of N-(2,6-dimethylphenyl)-3-bromopropanamide (1 g, 4.5 mmol) and N-carbobenzyloxypiperazine (1.7 g, 6.8 mmol) in 10 mL of acetone was added potassium carbonate (0.93 g, 6.8 mmol). The mixture was refluxed for 24 hours. The mixture was filtered, and the solvent was removed from the filtrate under reduced pressure. The residue was purified using column chromatography, to provide N-(2, 6-dimethylphenyl)-3-(4-carbobenzyloxypiperazinyl)propanamide, a compound of formula (3).

Step 2—Preparation of a Compound of Formula (4)

To N-(2,6-dimethylphenyl)-3-(4-carbobenzyloxypiperazinyl)propanamide (1.3 g) in 10 mL of methanol was added 10% Pd/C, and the mixture was hydrogenated at 30 psi for 24 hours. The mixture was filtered, and the solvent was removed from the filtrate under reduced pressure, to afford N-(2,6-dimethylphenyl)-3-piperazinylpropanamide, a compound of formula (4),which was used without further purification.

Step 3—Preparation of a Compound of Formula I

A mixture of N-(2,6-dimethylphenyl)-3-piperazinylpropanamide (0.15 g, 0.57 mmol) and 2-methyl-5-(oxiran-2-ylmethoxy)benzothiazole (0.127 g, 0.57 mmol) in 8 mL of ethanol was refluxed for 24 hours. The solvent was removed under reduced pressure, and the residue was purified using preparative TLC.

B. Preparation of Other Compounds of Formula I

Similarly, following the procedure of 5A above, but optionally replacing N-(2,6-dimethylphenyl)-3-piperazinylpropanamide with other compounds of formula (4), and optionally replacing 2-methyl-5-(oxiran-2-ylmethoxy)benzothiazole with other compounds of formula (5), the following compounds of Formula I were prepared:

3-{4-[(2S)-2-hydroxy-3-(2-methylbenzothiazol-5-yloxy)propyl]piperazinyl}-N-(2,6-dimethylphenyl)propanamide;

N-(2,6-dimethylphenyl)-3-{4-[2-hydroxy-3-(2-methoxyphenoxy)-propyl]piperazinyl}propanamide; and 3-{4-[(2S)-2-hydroxy-3-(2-methylbenzothiazol-5-yloxy)propyl]-2,5-dimethylpiperazinyl}-N-(2,6-dimethylphenyl)propanamide.

C. Preparation of Other Compounds of Formula I

Similarly, following the procedure of 5A above, but optionally replacing N-(2,6-dimethylphenyl)-3-piperazinylpropanamide with other compounds of formula (4), and optionally replacing 2-methyl-5-(oxiran-2-ylmethoxy)benzothiazole with other compounds of formula (5), other compounds of Formula I are prepared.

EXAMPLE 6

Preparation of a compound of Formula (15) in which R$^1$ is 4-Fluorophenyl, R$^{17}$ is Ethyl, and R$^{21}$ is Hydrogen

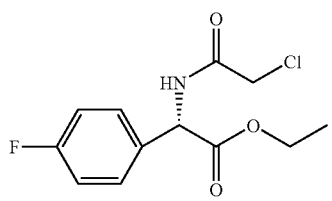

To ethyl (2S)-2-amino-2-(4-fluorophenyl)acetate (2.2 g, 9.4 mmol), a compound of formula (f) in tetrahydrofuran (20 mL) was added chloroacetic anhydride (1.0 g 6.3 mmol), diisopropylethylamine(3.3 ml 19.0 mmol) and the mixture stirred under nitrogen at room temperature overnight. The solvent was removed under reduced pressure, the residue dissolved in ethyl acetate (100 ml), washed three times with saturated aqueous sodium bicarbonate, and dried oversodium sulfate. The solvent removed in vacuo and ethyl (2S)-2-(2-chloroacetylamino)-2-(4-fluorophenyl)acetate, a compound of formula (1), was used without further purification.

EXAMPLE 7

Preparation of a Compound of Formula I in which R$^1$ is 4-Fluorophenyl, A is CH$_2$, R$^2$ is 2-Methylbenzothiazol-5-yl, R$^3$, R$^4$, R$^5$, R$^6$, R$^7$, R$^8$, and R$^{21}$ are Hydrogen, T is Oxygen, X$^1$ is —(CR$^{15}$R$^{16}$)—, in which R$^{15}$ is Hydrogen and R$^{16}$ is Carboxyethyl, and Y is —CH$_2$—

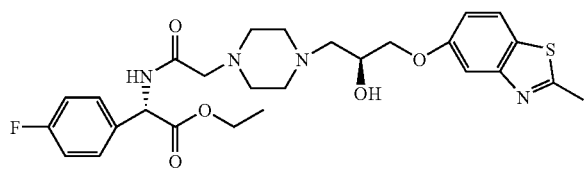

Ethyl (2S)-2-(2-chloroacetylamino)-2-(4-fluorophenyl)acetate (400 mg, 1.46 mmol), (2S)-3-(2-methylbenzothiazol-5-yloxy)-1-piperazinylpropan-2-ol (560 mg, 1.46 mmol), and 1.26 ml diisopropylethylamine (7.3 mmol) was refluxed in ethanol for 24 hours. Solvent was removed under reduced pressure, and the residue purified by Prep TLC, to provide ethyl (2S)-2-(2-{4-[(2S)-2-hydroxy-3-(2-methylbenzothiazol-5-yloxy)propyl]piperazinyl}acetylamino)-2-(4-fluorophenyl)acetate.

Similarly prepared were:

methyl (2R)-2-(2-{4-[(2S)-2-hydroxy-3-(2-methylbenzothiazol-5-yloxy)propyl]-piperazinyl}acetylamino)-2-phenylacetate;

ethyl 2-(2-{4-[2-hydroxy-3-(2-methylbenzothiazol-5-yloxy)propyl]-piperazinyl}acetylamino)-2-[4-(trifluoromethyl)phenyl]acetate;

ethyl 2-(2-{4-[(2S)-2-hydroxy-3-(2-methylbenzothiazol-5-yloxy)propyl]-piperazinyl}acetylamino)(2S)-2-(4-fluorophenyl)acetate;

2-(2-{4-[(2S)-2-hydroxy-3-(2-methylbenzothiazol-5-yloxy)propyl]-piperazinyl}acetylamino)(2S)-2-(4-fluorophenyl)acetic acid;

methyl 2-(2-{4-[(2S)-2-hydroxy-3-(2-methylbenzothiazol-5-yloxy)propyl]-piperazinyl}acetylamino)(2S)-2-cyclohexylacetate;

2-(2-{4-[(2S)-2-hydroxy-3-(2-methylbenzothiazol-5-yloxy)propyl]-piperazinyl}acetylamino)(2S)-2-phenylacetic acid; and 2-(2-{4-[2-hydroxy-3-(2-methylbenzothiazol-5-yloxy)propyl]piperazinyl}acetylamino)-2-[4-(trifluoromethyl)phenyl]acetic acid.

EXAMPLE 8

Preparation of a Compound of Formula (5)

A. Preparation of 2-(4-fluorophenyl)-5-methoxybenzoxazole

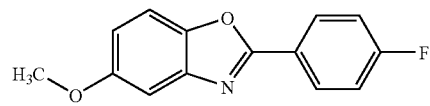

A mixture of 2-amino-4-methoxyphenol (3.07 g, 22.09 mmol) and 4-fluorobenzaldehyde (3.55 mL, 33.14 mmol) in 40 mL of methanol was stirred at 45° C. overnight. The solvent was evaporated under reduced pressure, and the residue was dissolved in methylene chloride (50 mL), to which was added DDQ (6.02 g, 26.51 mmol) slowly. The resulting mixture was stirred at room temperature for 45 minutes. The solvent was evaporated under reduced pressure, and to the residue was added 300 mL of ethyl acetate. The organic layer was washed sequentially with saturated sodium bicarbonate and brine, dried over sodium sulfate, and evaporated under reduced pressure. Column chromatography (ethyl acetate:Hexanes=1:9) gave 2-(4-fluorophenyl)-5-methoxybenzoxazole as a white solid.

B. Preparation of 2-(4-fluorophenyl)benzoxazol-5-ol

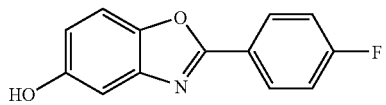

To a stirred solution of 2-(4-fluorophenyl)-5-methoxybenzoxazole (2.89 g, 11.89 mmol) in methylene chloride (70 mL) was added BBr₃ (1 M in CH₂Cl₂, 13.08 mL) dropwise in an ice-bath. The resulting mixture was stirred at room temperature for 36 hours. The solvent was evaporated under reduced pressure, and the residue was dissolved in ethyl acetate (150 mL). The organic layer was washed sequentially with saturated sodium bicarbonate and brine, dried over sodium sulfate, and evaporated under reduced pressure. Column chromatography (ethyl acetate:Hexanes=1:4) gave 2-(4-fluorophenyl)benzoxazol-5-ol as a white solid.

Reaction with epichlorohydrin provides a compound of formula (5).

EXAMPLE 9

A. Preparation of 2-Amino-4-methoxyphenol

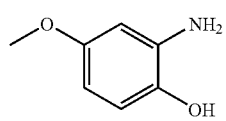

Commercially available 4-methoxy-2-nitrophenol (1 g, 5.9 mmol) was dissolved in 10 mL methanol, and 10% Pd/C was added to the mixture. The mixture was hydrogenated in a Parr™ shaker at 30 psi until consumption of hydrogen ceased. The mixture was filtered through Celite and concentrated under reduced pressure, to yield 2-amino-4-methoxyphenol.

B. Preparation of 2-(2,4-Dichlorophenyl)-5-methoxybenzoxazole

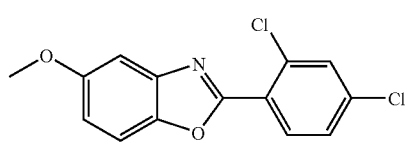

To a solution of 2-amino-4-methoxyphenol (1 g, 7.1 mmol), a compound of formula (j) in 20 mL MeOH was added (2,4-dichlorophenyl)formaldehyde (1.2 g, 7.1 mmol), a compound of formula (k). The mixture was heated at 45° C. for 12 hours. The mixture was concentrated under reduced pressure and the residue was dissolved in 50 mL dichloromethane. To the solution was added DDQ (1.7 g, 7.8 mmol), and the mixture was allowed to stir at room temperature for 30 minutes. The reaction mixture was then diluted with an additional 30 mL of dichloromethane and washed sequentially with saturated NaHCO₃ (2×50 mL) and brine. The organic layer was separated, dried over MgSO₄ and concentrated under reduced pressure to yield 2-(2,4-dichlorophenyl)-5-methoxybenzoxazole, a compound of formula (l), which was purified using flash column chromatography.

C. Synthesis of 2-(2,4-dichlorophenyl)benzoxazol-5-ol, a compound of formula (m)

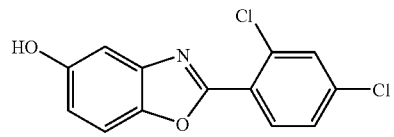

2-(2,4-dichlorophenyl)-5-methoxybenzoxazole (0.5 g, 1.7 mmol) was dissolved in 25 mL dichloromethane. To the solution was added boron tribromide (8 mmol) and the mixture was allowed to stir at room temperature for 48 hours. The mixture was then diluted with 25 mL dichloromethane and washed sequentially with saturated sodium bicarbonate (2×25 mL), followed by brine. The organic layer was separated, dried over MgSO₄ and filtered. The solvent was removed under reduced pressure, to provide 2-(2,4-dichlorophenyl)benzoxazol-5-ol, which was purified using flash chromatography.

EXAMPLE 10

Synthesis of 2-(2,4-Dichlorophenyl)-5-(oxiran-2-ylmethoxy)benzoxazole a Compound of Formula (5)

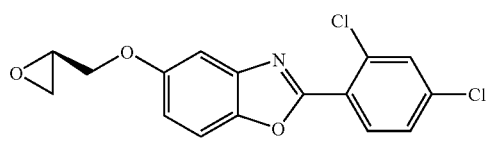

A mixture of 2-(2,4-dichlorophenyl)benzoxazol-5-ol (6.0 g, 36 mmol), (S)-(+)-epichlorohydrin (3.3 g, 315 mmol) (20 ml, 182 mmol), and potassium carbonate (20 g, 144 mmol) in acetone (100 ml) was heated to reflux and allowed to stir overnight. The solution was allowed to cool and filtered through Celite 512. The filtrate was evaporated under reduced pressure to yield an oil, which was chromatographed on silica gel, eluting with 20% ethyl acetate/hexanes, to yield 5-[((2R)oxiran-2-yl)methoxy]-2-(2,4-dichlorophenyl)benzoxazole as white solid (6.2 g, 28 mmol).

The following examples illustrate the preparation of representative pharmaceutical Formulations containing a compound of Formula I, such as those prepared in accordance with Example 4.

EXAMPLE 11

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules.

EXAMPLE 12

A tablet Formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 13

A dry powder inhaler Formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

EXAMPLE 14

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 15

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 16

Suspensions, each containing 50 mg of active ingredient per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 17

A subcutaneous Formulation may be prepared as follows:

| Ingredient | Quantity |
|---|---|
| Active Ingredient | 5.0 mg |
| Corn Oil | 1.0 mL |

EXAMPLE 18

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5-6) |
| water (distilled, sterile) | q.s. to 1.0 ml |
| Nitrogen Gas, NF | q.s. |

EXAMPLE 19

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C with stirring. A sufficient quantity of water at 60° C is then added with vigorous stirring to emulsify the ingredients, and water then added q.s. 100 g.

EXAMPLE 20

Sustained Release Composition

| Ingredient | Weight Range (%) |
| --- | --- |
| Active ingredient | 50-95 |
| Microcrystalline cellulose (filler) | 1-35 |
| Methacrylic acid copolymer | 1-35 |
| Sodium hydroxide | 0.1-1.0 |
| Hydroxypropyl methylcellulose | 0.5-5.0 |
| Magnesium stearate | 0.5-5.0 |

The sustained release Formulations of this invention are prepared as follows: Compound and pH-dependent binder and any optional excipients are intimately mixed(dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, for example sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets for example have a hardness sufficient to withstand 8 Kp compression. The tablet size will depend primarily upon the amount of compound in the tablet. The tablets will include from 300 to 1100 mg of compound free base. For example, the tablets will include amounts of compound free base ranging from 400-600 mg, 650-850 mg, and 900-1100 mg.

In order to influence the dissolution rate, the time during which the compound containing powder is wet mixed is controlled. For example the total powder mix time, i.e. the time during which the powder is exposed to sodium hydroxide solution, will range from 1 to 10 minutes and for example from 2 to 5 minutes. Following granulation, the particles are removed from the granulator and placed in a fluid bed dryer for drying at about 60° C.

EXAMPLE 21

Mitochondrial Assays

Rat heart mitochondria were isolated by the method of Nedergard and Cannon (Methods in Enzymol. 55, 3, 1979).

Palmitoyl CoA oxidation—The Palmityl CoA oxidation was carried out in a total volume of 100 micro liters containing the following agents: 110 mM KCl, 33 mM Tris buffer at pH 8, 2 mM KPi, 2 mM $MgCl_2$, 0.1 mM EDTA, 14.7 microM defatted BSA, 0.5 mM malic acid, 13 mM carnitine, 1 mM ADP, 52 micrograms of mitochondrial protein, and 16 microM 1-C14 palmitoyl CoA (Sp. Activity 60 mCi/mmole; 20 microCi/ml, using 5 microliters per assay). The compounds of this invention were added in a DMSO solution at the following concentrations: 100 micro molar, 30 micro molar, and 3 micro molar. In each assay, a DMSO control was used. After 15 min at 30° C., the enzymatic reaction was centrifuged (20,000 g for 1 min), and 70 microliters of the supernatant was added to an activated reverse phase silicic acid column (approximately 0.5 ml of silicic acid). The column was eluted with 2 ml of water, and 0.5 ml of the eluent was used for scintillation counting to determine the amount of $C^{14}$ trapped as $C^{14}$ bicarbonate ion.

The compounds of the invention showed activity as fatty acid oxidation inhibitors in this assay. Representative examples of test data are shown below, along with their NMR:

| Structure | PalmCoA $IC_{50}$ | $^1$H NMR, $CDCl_3$, 400 MHz |
| --- | --- | --- |
| (indane-NHC(O)CH2-piperazine-CH2CH(OH)CH2O-benzothiazole-Me) | .15 µM | 9.20(brs, 1H); 8.01(d, 1H); 7.69(d, 1H); 7.48(brs, 1H); 7.19(t, 1H); 7.08-6.99(m, 2H); 4.20-4.07(m, 1H); 4.06-4.01(m, 2H); 3.20(s, 2H); 2.98(t, 2H); 2.90-2.55 (m, 15H); 2.18(quintet, 2H). |

| Structure | PalmCoA IC$_{50}$ | $^1$H NMR, CDCl$_3$, 400 MHz |
|---|---|---|
| (4-phenoxyphenyl)-NHC(O)CH$_2$-piperazine-CH$_2$CH(OH)CH$_2$O-(2-Me-benzothiazol-5-yl) | 0.33 μM | 7.70(d, 1H); 7.57(d, 2H); 7.42(d, 1H); 7.40-7.29(m, 4H); 7.16-6.96(m, 4H); 4.30-4.20(m, 1H); 4.18-4.02(m, 2H); 3.20(s, 2H); 2.99-2.63(m, 13H). |
| (3-phenoxyphenyl)-NHC(O)CH$_2$-piperazine-CH$_2$CH(OH)CH$_2$O-(2-Ph-benzoxazol-5-yl) | 8.5 μM | 8.23-8.19(d, 2H); 7.60-7.54(m, 3H); 7.51(d, 1H); 7.40-7.25(m, 6H); 7.17(t, 1H); 7.02(m, 3H); 6.78(m, 1H); 4.22-4.16(m, 1H); 4.16-4.04(m, 2H); 3.18(s, 2H); 2.81-2.59(m, 10H). |
| (3-phenylphenyl)-NHC(O)CH$_2$-piperazine-CH$_2$CH(OH)CH$_2$O-(2-Me-benzothiazol-6-yl) | 0.18 μM | 7.78(brs, 1H); 7.74(d, 1H); 7.72-7.58(m, 3H); 7.43-7.30(m, 6H); 7.07(dd, 1H); 4.21-4.17(m, 1H); 4.15-4.00(m, 2H); 3.20(s, 2H); 2.83-2.58(m, 13H). |
| (9-Et-carbazol-3-yl)-NHC(O)CH$_2$-piperazine-CH$_2$CH(OH)CH$_2$O-(2-Me-benzothiazol-5-yl) | 0.85 μM | 9.20(s, 1H); 8.38(s, 1H); 8.10(d, 1H); 7.64(d, 1H); 7.60(d, 1H); 7.45(m, 2H); 7.40(m, 2H); 7.20(m, 1H); 7.05(dd, 1H); 4.40(m, 2H); 4.20(m, 1H); 4.05(m, 2H); 3.20(s, 2H); 2.80(s, 3H); 2.80-2.60(m, 10H); 1.40(t, 3H). |
| (quinolin-6-yl)-NHC(O)CH$_2$-piperazine-CH$_2$CH(OH)CH$_2$O-(2-Ph-benzoxazol-5-yl) | 6.2 μM | (CD$_3$OD solvent): 8.79(dd, 1H); 8.44(d, 1H); 8.34(d, 1H); 8.25(dd, 2H); 8.03(d, 1H); 7.90(dd, 1H); 7.59-7.66(m, 4H); 7.30-7.40(m, 1H); 7.12(td, J=6.06, 3.13 Hz, 1H); 4.28-4.19(m, 1H); 4.19-4.13(m, 1H); 4.13-4.03(m, 1H); 3.31(s, 2H); 2.85-2.66(m, 10H). |
| (quinolin-8-yl)-NHC(O)CH$_2$-piperazine-CH$_2$CH(OH)CH$_2$O-(2-Me-benzothiazol-6-yl) | 5.2 μM | 8.80(d, 2H); 8.01(d, 1H); 8.84(d, 1H); 7.74-7.62(m, 2H); 7.59(t, 1H); 7.43(brs, 1H); 4.30-4.20(m, 1H); 4.08(d, 2H); 3.29(s, 2H); 3.03-2.60(m, 13H). |
| (4-(4-Cl-phenyl)-thiazol-2-yl)-NHC(O)CH$_2$-piperazine-CH$_2$CH(OH)CH$_2$O-(2-Me-benzothiazol-5-yl) | 7.0 μM | 10.30(brs, 1H); 7.80(d, 2H); 7.69(d, 1H); 7.47(brs, 1H); 7.39(d, 2H); 7.18(s, 1H); 7.02(dd, 1H); 4.20-4.10(m, 1H); 4.10-4.03(m, 2H); 3.23(s, 2H); 3.08-2.98(m, 2H); 2.81-2.75(m, 6H); 2.60-2.40(m, 3H); 2.30(t, 1H); 1.14(d, 3H). |
| (4-(4-Cl-phenyl)-thiazol-2-yl)-NHC(O)CH$_2$-(3-Me-piperazine)-CH$_2$CH(OH)CH$_2$O-(2-Me-benzothiazol-5-yl) | 0.40 μM | 10.30(brs, 1H); 7.80(d, 2H); 7.69(d, 1H); 7.47(brs, 1H); 7.39(d, 2H); 7.18(s, 1H); 7.02(dd, 1H); 4.23-4.17(m, 1H); 4.15-4.04(m, 2H); 3.30(s, 2H); 2.98-2.60(m, 13H). |
| (1S-tetrahydronaphthalen-1-yl)-NHC(O)CH$_2$-piperazine-CH$_2$CH(OH)CH$_2$O-(2-Me-benzothiazol-5-yl) | 0.08 μM | 7.66(d, 1H); 7.42(brs, 1H); 7.38(brd, 1H); 7.35-7.10(m, 3H); 7.01(dd, 1H); 5.20(dd, 1H); 4.18-4.09(m, 1H); 4.08-3.99(m, 2H); 3.10(d, 2H); 2.90-2.40(m, 15H); 2.18-2.06(m, 1H); 1.90-1.70(m, 2H). |

| Structure | PalmCoA IC$_{50}$ | $^1$H NMR, CDCl$_3$, 400 MHz |
|---|---|---|
| [Structure: (R)-1-(naphthalen-2-yl)ethyl-NH-C(O)-CH$_2$-piperazine-CH$_2$-CH(OH)-CH$_2$-O-benzothiazole-Me] | 0.85 μM | 7.80(m, 3H); 7.70(s, 1H); 7.60(d, 1H); 7.40(m, 4H); 6.97(d, 1H); 5.25(m, 1H); 4.05(m, 1H); 4.00(m, 2H); 3.42 (s, 1H); 3.38(s, 1H); 3.00(q, 2H); 2.78 (s, 3H); 2.60-2.40(m, 8H); 1.45(d, 3H). |
| [Structure: (R)-1-phenylethyl-NH-C(O)-CH$_2$-piperazine-CH$_2$-CH(OH)-CH$_2$-O-benzothiazole-Me] | 4.4 μM | 7.60(d, 1H); 7.39(brs, 1H); 7.38-7.17 (m, 5H); 5.08(quintet, 1H); 4.18-4.05 (m, 1H); 4.00-3.91(d, 2H); 2.99(dd, 2H); 2.78(s, 3H); 2.78-2.40(m, 10H); 1.42(d, 3H). |

EXAMPLE 22

Perfusate

Langendorff perfusion was conducted using a Krebs-Henseleit solution containing: (mM) NaCl (118.0), KCl (4.7), KH$_2$PO$_4$ (1.2), MgSO$_4$ (1.2), CaCl$_2$ (2.5), NaHCO$_3$ (25.0) and glucose (5.5 or 11) (Finegan et al. 1996). The working heart perfusate consisted of a Krebs-Henseleit solution with the addition of palmitate (0.4 or 1.2 mM) pre-bound to 3% bovine serum albumin (essentially fatty acid free BSA) and insulin (100 μU/ml). Palmitate was initially dissolved in an ethanol:water mixture (40%:60%) containing 0.5-0.6 g Na$_2$CO$_3$ per g of palmitate. Following heating to evaporate the ethanol, this mixture was then added to the 3% BSA-Krebs-Henseleit mixture (without glucose) and allowed to dialyze (8000 MW cut-off) overnight in 10 volumes of glucose-free Krebs-Henseleit solution. The next day, glucose was added to the solution and the mixture was filtered through glass microfiber filters (GF/C, Whatman, Maidstone, England) and kept on ice, or refrigerated, prior to use. The perfusate was continuously oxygenated with a 95% CO$_2$, 5% O$_2$ gas mixture while in the perfusion apparatus to main aerobic conditions.

EXAMPLE 23

Heart Perfusion Protocols

Rats were anesthetized with pentobarbital (60 mg/kg, intraperitoneally) and hearts were rapidly removed and placed in ice-cold Krebs-Henseleit solution. The hearts were then rapidly cannulated via the aortic stump and Langendorff perfusion at constant pressure (60 mm Hg) was initiated and continued for a 10-min equilibration period. During this equilibration period, the pulmonary artery was cut, and excess fat and lung tissue removed to reveal the pulmonary vein. The left atrium was cannulated and connected to the preload line originating from the oxygenation chamber. After the 10-min equilibration period, hearts were switched to working mode (by clamping off the Langendorff line and opening the preload and afterload lines) and perfused at 37° C. under aerobic conditions at a constant left atrial preload (11.5 mm Hg) and aortic afterload (80 mm Hg). The compliance chamber was filled with air adequate to maintain developed pressure at 50-60 mm Hg. Perfusate was delivered to the oxygenation chamber via a peristaltic pump from the reservoir chamber that collected aortic and coronary flows as well as overflow from the oxygenator.

Typically, hearts were perfused under aerobic conditions for 60 min. Hearts were paced at 300 beats/min throughout each phase of the perfusion protocol (voltage adjusted as necessary) with the exception of the initial 5 min of reperfusion when hearts were allowed to beat spontaneously.

At the end of the perfusion protocol, hearts were rapidly frozen using Wollenberger clamps cooled to the temperature of liquid nitrogen. Frozen tissues were pulverized and the resulting powders stored at –80° C.

EXAMPLE 24

Myocardial Mechanical Function

Aortic systolic and diastolic pressures were measured using a Sensonor (Horten Norway) pressure transducer attached to the aortic outflow line and connected to an AD Instruments data acquisition system. Cardiac output, aortic flow and coronary flow (cardiac output minus aortic flow) were measured (ml/min) using in-line ultrasonic flow probes connected to a Transonic T206 ultrasonic flow meter. Left ventricular minute work (LV work), calculated as cardiac output×left ventricular developed pressure (aortic systolic pressure–preload pressure), was used as a continuous index of mechanical function. Hearts were excluded if LV work decreased more than 20% during the 60-min period of aerobic perfusion.

EXAMPLE 25

Myocardial Oxygen Consumption and Cardiac Efficiency

Measuring the atrial-venous difference in oxygen content of the perfusate and multiplying by the cardiac output provides an index of oxygen consumption. Atrial oxygen content (mmHg) was measured in perfusate in the preload line or just prior to entering the left atria. Venous oxygen content was measured from perfusate exiting the pulmonary artery and passing through in-line O$_2$ probes and meters Microelectrodes Inc., Bedford, N.H. Cardiac efficiency was calculated as the cardiac work per oxygen consumption.

EXAMPLE 26

Measurement of Glucose and Fatty Acid Metabolism

Determining the rate of production of $^3$H$_2$O and $^{14}$CO$_2$ from [$^3$H/$^{14}$C]glucose in the isolated working rat model allows a direct and continuous measure of the rates of glycolysis and glucose oxidation. Alternatively, the measure of the production of $^3$H$_2$O from [5-$^3$H]palmitate provides a direct and continuous measure of the rate of palmitate oxidation.

Dual labelled substrates allows for the simultaneous measure of either glycolysis and glucose oxidation or fatty acid oxidation and glucose oxidation. A 3-ml sample of perfusate was taken from the injection port of the recirculating perfusion apparatus at various time-points throughout the protocol for analysis of $^3H_2O$ and $^{14}CO_2$ and immediately placed under mineral oil until assayed for metabolic product accumulation. Perfusate was supplemented with [$^3H/^{14}C$]glucose or [5-$^3H$] palmitate to approximate a specific activity of 20 dpm/mmol. Average rates of glycolysis and glucose oxidation were calculated from linear cumulative time-courses of product accumulation between 15 and 60 min for aerobic perfusion. Rates of glycolysis and glucose oxidation are expressed as µmol glucose metabolized/min/g dry wt.

EXAMPLE 27

Measurement of Myocardial Glycolysis

Rates of glycolysis were measured directly as previously described (Saddik & Lopaschuk, 1991) from the quantitative determination of $^3H_2O$ liberated from radiolabeled [5-$^3H$] glucose at the enolase step of glycolysis. Perfusate samples were collected at various time-points throughout the perfusion protocol. $^3H_2O$ was separated from the perfusate by passing perfusate samples through columns containing Dowex 1-X 4 anion exchange resin (200-400 mesh). A 90 g/L Dowex in 0.4 M potassium tetraborate mixture was stirred overnight after which 2 ml of the suspension was loaded into separation columns and washed extensively with $dH_2O$ to remove the tetraborate. The columns were found to exclude 98-99.6% of the total [$^3H$]glucose (Saddik & Lopaschuk, 1996). Perfusate samples (100 µl) were loaded onto the columns and washed with 1.0 ml $dH_2O$. Effluent was collected into 5 ml of Ecolite Scintillation Fluid (ICN, Radiochemicals, Irvine, Calif.) and counted for 5 min in a Beckman LS 6500 Scintillation Counter with an automatic dual ($^3H/^{14}C$) quench correction program. Average rates of glycolysis for each phase of perfusion are expressed as µmol glucose metabolized/min/g dry wt as described above.

EXAMPLE 28

Measurement of Myocardial Glucose Oxidation

Glucose oxidation was also determined directly as previously described (Saddik & Lopaschuk, 1991) by measuring $^{14}CO_2$ from [$^{14}C$]glucose liberated at the level of pyruvate dehydrogenase and in the Krebs cycle. Both $^{14}CO_2$ gas exiting the oxygenation chamber and [$^{14}C$]bicarbonate retained in solution were measured. Perfusate samples were collected at various time-points throughout the perfusion protocol. $^{14}CO_2$ gas was collected by passing the gas exiting the oxygenator through a hyamine hydroxide trap (20-50 ml depending on perfusion duration). Perfusate samples (2×1 ml), which were stored under oil to prevent the escape of gas by equilibration with atmospheric $CO_2$, were injected into 16×150 mm test tubes containing 1 ml of 9 N $H_2SO_4$. This process releases $^{14}CO_2$ from the perfusate present as $H^{14}CO_3^-$. These duplicate tubes were sealed with a rubber stopper attached to a 7-ml scintillation vial containing a 2×5 cm piece of filter paper saturated with 250 □l of hyamine hydroxide. The scintillation vials with filter papers were then removed and Ecolite Scintillation Fluid (7 ml) added. Samples were counted by standard procedures as described above. Average rates of glucose oxidation for each phase of perfusion are expressed as µmol glucose metabolized/min/g dry wt as described above.

EXAMPLE 29

Measurement of Myocardial Fatty Acid Oxidation

Rates of palmitate oxidation were measured directly as previously described (Saddik & Lopaschuk, 1991) from the quantitative determination of $^3H^-H_2O$ liberated from radiolabeled [5-$^3H$]palmitate. $^3H_2O$ was separated from [5-$^3H$] palmitate following a chloroform:methanol (1.88 ml of 1:2 v/v) extraction of a 0.5 ml sample of buffer then adding 0.625 ml of chloroform and 0.625 ml of a 2M KCL:HCl solution. The aqueous phase was removed and treated with a mixture of chloroform, methanol and KCl:HCl (1:1:0.9 v/v). Duplicate samples were taken from the aqueous phase for liquid scintillation counting and rates of oxidation were determined taking into account a dilution factor. This results in >99% extraction and separation of $^3H_2O$ from [5-$^3H$]palmitate. Average rates of glucose oxidation for each phase of perfusion are expressed as µmol glucose metabolized/min/g dry wt as described above.

Dry to Wet Ratios

Frozen ventricles were pulverized at the temperature of liquid nitrogen with a mortar and pestle. Dry to wet determinations were made by weighing a small amount of frozen heart tissue and re-weighing that same tissue after 24-48 hr of air drying and taking the ratio of the two weights. From this ratio, total dry tissue could be calculated. This ratio was used to normalize, on a per g dry weight basis, rates of glycolysis, glucose oxidation and glycogen turnover as well as metabolite contents.

The compounds of the invention showed activity as fatty acid oxidation inhibitors in this assay.

What is claimed is:

1. A compound of the formula:

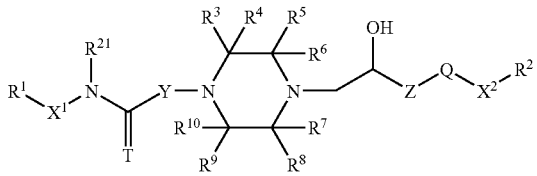

wherein:
R$^1$ is aryl or cycloalkyl optionally substituted with 1 to 3 substituents selected from alkyl, hydroxy, alkoxy, halogen, halogen substituted alkyl, phenyl, and phenyl substituted with alkyl, alkoxy, hydroxy, halogen, or CF$_3$;
R$^2$ is benzoxazolyl or benzothiazolyl optionally substituted with 1 to 3 substituents selected from alkyl, hydroxy, alkoxy, halogen, halogen substituted alkyl, phenyl, and phenyl substituted with alkyl, alkoxy, hydroxy, halogen, or CF$_3$;
X$^1$ is —(CR$^{15}$R$^{16}$)$_p$—, in which R$^{15}$ and R$^{16}$ are independently hydrogen, hydroxy, lower alkyl, or —C(O)OR$^{17}$, in which R$^{17}$ is hydrogen, lower alkyl, or phenyl, or phenyl substituted with alkyl, alkoxy, hydroxy, halogen, or CF$_3$, and p is 1, 2 or 3;
with the proviso that when p is 1, R$^{15}$ and R$^{16}$ cannot be hydroxy;
R$^{21}$ is hydrogen or lower alkyl;
T is oxygen or sulfur;
Y and Z are —(CR$^{18}$R$^{19}$)$_q$— and q at each occurrence is 1, 2 or 3, in which R$^{18}$ and R$^{19}$ at each occurrence is hydrogen or lower alkyl; and R³, R⁴, R⁵, R⁶, R⁷, R⁸, R⁹, and R¹⁰ at each occurrence are hydrogen, lower alkyl, or —C(O)R, in which R is —OR¹¹ or —NR¹¹R¹², where R¹¹ and R¹² are hydrogen or lower alkyl; or R³ and R⁴, R⁵ and R⁶, R⁷ and R⁸, R⁹ and R¹⁰, when taken together with the carbon to which they are attached, represent carbonyl;

Q is oxygen, sulfur, or —NR²⁰—, in which R²⁰ is hydrogen or optionally substituted lower alkyl; and X² is a covalent bond or —(CR¹⁸R¹⁹)$_q$— wherein q at each occurrence is 1, 2 or 3, and R¹⁸ and R¹⁹ at each occurrence is hydrogen or lower alkyl.

2. The compound of claim 1, wherein R³, R⁴, R⁵, R⁶, R⁷, R⁸, R⁹, and R¹⁰ at each occurrence are hydrogen and R⁵ is hydrogen or methyl.

3. The compound of claim 2, wherein Q and T are both oxygen and X² is a covalent bond.

4. The compound of claim 3, wherein R²¹ is hydrogen, Y is methylene or ethylene, and Z is methylene.

5. The compound of claim 4, wherein R¹ is optionally substituted aryl.

6. The compound of claim 5, wherein R¹ is naphth-2-yl, R² is 2-methylbenzothiazol-5-yl, R⁵ is hydrogen, and X¹ is —CH(CH₃)—, namely 2-{4-[(2R)-2-hydroxy-3-(2-methyl-benzothiazol-5-yloxy)propyl]piperazinyl}-N-((1S)-1-(2-naphthyl)ethyl)acetamide.

7. The compound of claim 5, wherein R¹ is phenyl, R² is 2-methylbenzothiazol-5-yl, R⁵ is hydrogen, and X¹ is —CH(CH₃)—, namely 2-{4-[(2R)-2-hydroxy-3-(2-methylbenzothiazol-5-yloxy)propyl]piperazinyl}-N-((1S)-1-phenylethyl)acetamide.

8. A method of treating a disease state chosen from diabetes, damage to skeletal muscles resulting from trauma or shock, and a cardiovascular disease selected from the group consisting of atrial arrhythmia, intermittent claudication, ventricular arrhythmia, Prinzmetal's (variant) angina, stable angina, unstable angina, congestive heart disease, and myocardial infarction in a mammal by administration of a therapeutically effective dose of a compound of claim 1.

9. The method of claim 8, wherein the disease state is a cardiovascular disease selected from atrial arrhythmia, intermittent claudication, ventricular arrhythmia, Prinzmetal's (variant) angina, stable angina, unstable angina, congestive heart disease, and myocardial infarction.

10. The method of 8, wherein the disease state is diabetes.

11. A pharmaceutical composition comprising at least one pharmaceutically acceptable excipient and a therapeutically effective amount of a compound of claim 1.

\* \* \* \* \*